(12) United States Patent
Lee et al.

(10) Patent No.: US 10,269,453 B2
(45) Date of Patent: Apr. 23, 2019

(54) METHOD AND APPARATUS FOR PROVIDING MEDICAL INFORMATION

(71) Applicant: SAMSUNG ELECTRONICS CO., LTD., Suwon-si (KR)

(72) Inventors: Woong Lee, Suwon-si (KR); Jae-chool Lee, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1005 days.

(21) Appl. No.: 14/302,960

(22) Filed: Jun. 12, 2014

(65) Prior Publication Data

US 2014/0372136 A1 Dec. 18, 2014

(30) Foreign Application Priority Data

Jun. 12, 2013 (KR) ........................ 10-2013-0067303

(51) Int. Cl.
*G06F 19/00* (2018.01)
*G16H 40/63* (2018.01)

(52) U.S. Cl.
CPC ............. *G16H 40/63* (2018.01); *G06F 19/00* (2013.01)

(58) Field of Classification Search
CPC .................... G06Q 50/22; G06Q 50/24; G06F 19/322–19/327
See application file for complete search history.

(56) References Cited

U.S. PATENT DOCUMENTS

| | | | | |
|---|---|---|---|---|
| 5,748,907 | A * | 5/1998 | Crane | G06Q 10/06 705/2 |
| 7,202,838 | B2* | 4/2007 | Kerr | G06F 19/321 345/1.2 |
| 7,636,365 | B2 | 12/2009 | Chang et al. | |
| 8,338,810 | B2 | 12/2012 | Hoernig | |
| 2002/0032583 | A1* | 3/2002 | Joao | G06F 19/328 705/2 |
| 2006/0052684 | A1* | 3/2006 | Takahashi | A61B 90/36 600/407 |
| 2010/0053213 | A1 | 3/2010 | Ishida et al. | |
| 2010/0064374 | A1* | 3/2010 | Martin | G16H 40/63 726/27 |

(Continued)

FOREIGN PATENT DOCUMENTS

| | | |
|---|---|---|
| EP | 2422702 A1 | 2/2012 |
| EP | 2468189 A1 | 6/2012 |

(Continued)

OTHER PUBLICATIONS

Communication dated Mar. 31, 2015 issued by the Korean Intellectual Property Office in counterpart Korean Patent Application No. 10-2013-67303.

(Continued)

*Primary Examiner* — Neal Sereboff
(74) *Attorney, Agent, or Firm* — Sughrue Mion, PLLC

(57) ABSTRACT

Provided are a method and apparatus for providing medical information. The method includes obtaining diagnostic information related to an object, setting an information providing area on which the diagnostic information is to be displayed on a console room window, the console room window being a transparent display unit, and displaying the diagnostic information on the information providing area of the console room window.

73 Claims, 29 Drawing Sheets

(56) References Cited

U.S. PATENT DOCUMENTS

2011/0248193 A1    10/2011   Goldstein et al.
2012/0163544 A1    6/2012   Mizrahi et al.

FOREIGN PATENT DOCUMENTS

| JP | 9-33856 A | 2/1997 |
| JP | 2004-180834 A | 7/2004 |
| JP | 2010-057528 A | 3/2010 |
| JP | 2012-135619 A | 7/2012 |
| KR | 10-2004-0075312 A | 8/2004 |
| KR | 10-2004-0077609 A | 9/2004 |

OTHER PUBLICATIONS

Communication dated Jun. 12, 2015 issued by the Korean Intellectual Property Office in counterpart Korean Patent Application No. 10-2013-67303.
International Search Report for PCT/KR2014/005128 dated Sep. 18, 2014 [PCT/ISA/210].
Written Opinion for PCT/KR2014/005128 dated Sep. 18, 2014 [PCT/ISA/237].
Communication from the Korean Intellectual Property Office dated Sep. 17, 2014, in a counterpart Korean application No. 10-2013-0067303.
Communication dated Jan. 10, 2017, issued by the European Patent Office in counterpart European application No. 14810295.7.
Communication dated Jun. 8, 2018, issued by the European Patent Office in counterpart European Application No. 14810295.7.

\* cited by examiner

METHOD AND APPARATUS FOR PROVIDING MEDICAL INFORMATION

CROSS-REFERENCE TO RELATED PATENT APPLICATION

This application claims priority from Korean Patent Application No. 10-2013-0067303, filed on Jun. 12, 2013, in the Korean Intellectual Property Office, the disclosure of which is incorporated herein in its entirety by reference.

BACKGROUND

1. Field

Apparatuses and methods consistent with exemplary embodiments relate to a method and an apparatus for providing a user with medical information generated when an object is diagnosed.

2. Description of the Related Art

A computer tomography (CT) system captures and synthesizes a plurality of x-ray images of an object while rotating about at least one axis. The CT system is widely used because the CT system provides cross-sectional images of the object such that internal structures of the object shown in the images do not overlap, unlike a general x-ray imaging system.

A magnetic resonance imaging (MRI) system exposes atomic nuclei in a body to a magnetic field and creates an image by using information obtained through resonance of the atomic nuclei. The MRI system is noninvasive, produces pictures with a higher contrast between tissues than the CT system, and also produces pictures with no artifacts at bone tissues. Also, the MRI system is widely used because the MRI system may capture various cross-sectional images in desired directions without changing a position of the object.

In the CT system or the MRI system, a console room in which a user is located is shielded from a shield room in which the object is located. A plurality of display devices and user interface devices for diagnosing the object are located in the console room.

Accordingly, the user may not efficiently use a space of the console room. Also, when the user performs multiple tasks at the same time, the user may not sufficiently observe the object through a console room window between the console room and the shield room.

SUMMARY

One or more exemplary embodiments provide a method and an apparatus for efficiently providing medical information by using a console room window. One or more exemplary embodiments also provide a computer-readable recording medium having embodied thereon a program for executing the method.

According to an aspect of an exemplary embodiment, there is provided a method of providing medical information, the method including: obtaining diagnostic information related to an object; setting an information providing area on which the diagnostic information is to be displayed on a console room window, the console room window being a transparent display unit; and displaying the diagnostic information on the information providing area of the console room window.

The setting may include setting at least one from among a size and a position of the information providing area, and the displaying includes displaying the diagnostic information based on the at least one from among the set size and the set position.

The method may further include setting on the console room window an observation area through which the console room window is observed.

The setting may include setting at least a part of the observation area as the information providing area.

The setting may include setting an area of the console room window other than the observation area as the information providing area.

The setting may include: selecting at least one from among a plurality of sub-areas of the console room window; and setting the selected at least one sub-area as the information providing area.

The console room window may include a plurality of transparent display units arranged adjacent to one another, wherein the setting includes matching at least one from among the plurality of transparent display units to the information providing area.

The information providing area may include a plurality of information providing areas, wherein the method further includes determining priorities of the plurality of information providing areas, wherein the displaying includes displaying a plurality of diagnostic information on the plurality of information providing areas based on at least one from among the priorities of the plurality of information providing areas and orders in which the plurality of diagnostic information are obtained.

The displaying the diagnostic information may include determining the plurality of information providing areas on which the plurality of diagnostic information are to be displayed according to importance of the plurality of diagnostic information.

The information providing area may include a plurality of information providing areas, wherein the method further includes determining priorities of the plurality of information providing areas, wherein the displaying includes displaying a plurality of diagnostic information on the plurality of information providing areas based on at least one from among the priorities of the plurality of information providing areas and importance of the plurality of diagnostic information.

The setting may include setting the information providing area based on a user input.

The user input may be received by using at least one from among a voice recognition sensor, a motion detection sensor, a touch sensor, and a pointing device recognition sensor.

The displaying may include adjusting a transparency of the diagnostic information based on at least one from among a value of the diagnostic information and a user input.

The adjusting may include adjusting the transparency of the diagnostic information based on a type of the diagnostic information.

The adjusting may include adjusting the transparency of the diagnostic information based on a position at which the diagnostic information is displayed on the console room window.

The method may further include detecting at least one from among a position of a user and a distance of the user from the console room window.

The displaying may include adjusting a size of the information providing area on which the diagnostic information is displayed based on the distance of the user from the console room window.

The displaying may include adjusting at least one from among a position and a size of the information providing area on which the diagnostic information is displayed on the console room window based on the position of the user.

The adjusting may include reducing the size of the information providing area in response to the detected position of the user which is closer to the information providing area.

The information providing area may include a plurality of information providing areas, wherein the method further includes determining priorities of the plurality of information providing areas, wherein the determining includes determining the priorities based the position of the user, wherein the displaying includes displaying a plurality of diagnostic information on the plurality of information providing areas based on the determined priorities.

The setting may include setting a substantially entire portion of the console room window as the information providing area.

The method may further include: capturing an image of an inner area of a shield room in which the object is located; and displaying the image of the inner area of the shield room on at least a portion of the information providing area.

The diagnostic information may include an image obtained by photographing at least a part of the object.

The diagnostic information may include an image obtained by photographing a movement of a diagnostic table on which the object is placed.

The diagnostic information may include a medical image of the object.

The diagnostic information may include an image obtained by photographing an inner area of a gantry in which the object is positioned.

The diagnostic information may include a message indicating that a movement of the object is detected, the message being generated in response to an amount of a detected movement of the object which is equal to or greater than a preset value.

The diagnostic information may include information about a local memory configured to store the diagnostic information.

The diagnostic information may include information about a state of progress of a protocol used in the object.

The diagnostic information may include personal information of the object.

The diagnostic information may include a list of patients including the object.

The diagnostic information may include a control menu for controlling a medical system configured to obtain the diagnostic information of the object.

The diagnostic information may include a communication guide menu configured to provide information about communication with an external network, wherein the method further includes performing the communication the external network based on a user input on the communication guide menu.

The diagnostic information may include bio-monitoring information about at least a predetermined part of the object.

The displaying may include displaying the bio-monitoring information on at least a portion of the information providing area corresponding to the at least a predetermined part of the object.

The obtaining may include obtaining the diagnostic information using a medical system comprising at least one from among a magnetic resonance imaging (MRI) system and a computed tomography (CT) system.

According to an aspect of another exemplary embodiment, there is provided an apparatus for providing medical information, the apparatus including: a diagnostic information obtaining unit configured to obtain diagnostic information related to an object; an area setting unit configured to set an information providing area on which the diagnostic information is to be displayed on a console room window, the console room window being a transparent display unit; and a controller configured to control the console room window to display the diagnostic information on the information providing area.

According to an aspect of still another exemplary embodiment, there is provided a computer-readable recording medium having embodied thereon a program for executing the method.

According to an aspect of still another exemplary embodiment, there is provided an information providing apparatus including: at least one processor operable to read and operate according to instructions within a computer program; and at least one memory operable to store at least portions of said computer program for access by said processor; wherein said computer program includes algorithms to cause said processor to implement: a communicator configured to receive information related to an object from an external apparatus; a display configured to display the received information; and a controller configured to set at least a portion of the display as a transparent area through which the object is viewable based on at least one of a type of the received information and a user command, wherein the received information comprises at least one information obtained by sensing at least a part of the object.

BRIEF DESCRIPTION OF THE DRAWINGS

The above and/or other aspects will become more apparent by describing in detail certain exemplary embodiments with reference to the attached drawings, in which.

DETAILED DESCRIPTION

Figure 1:
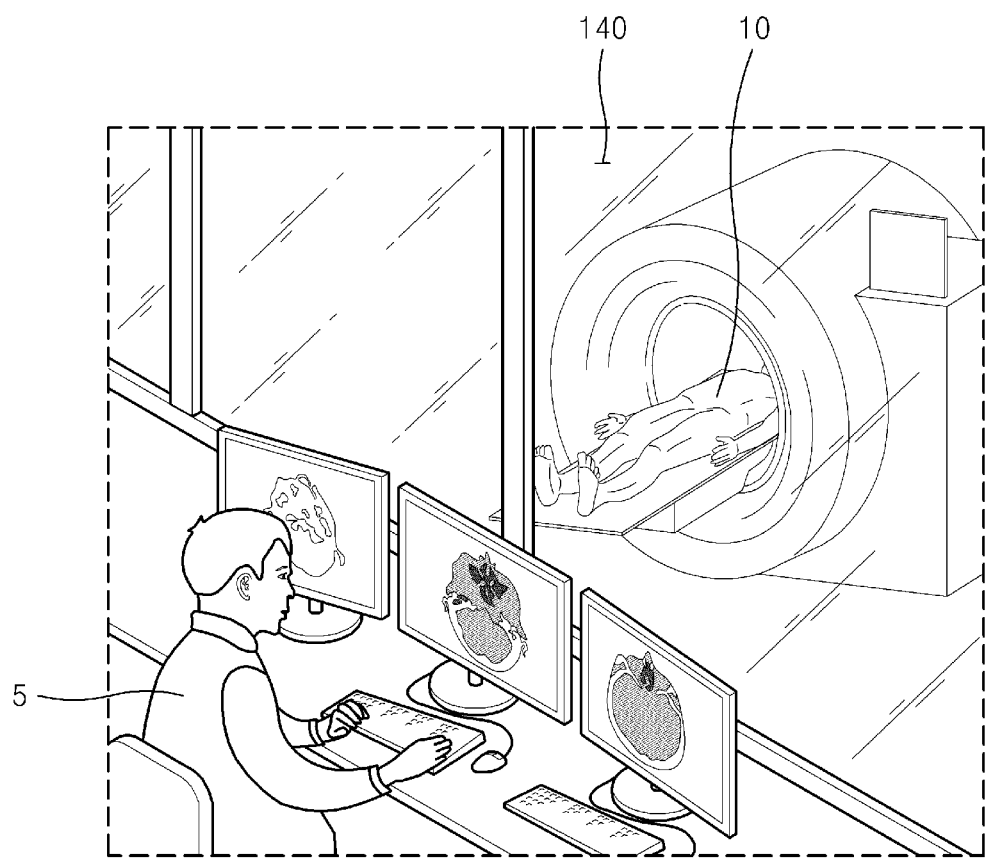
FIG. 1 is a view for explaining general technologies and content related to exemplary embodiments.

Most of the terms used herein are general terms that have been widely used in the technical art to which the present disclosure pertains. However, some of the terms used herein may be created by reflecting the intentions of technicians in this art, precedents, or new technologies. Also, some of the terms used herein may be arbitrarily chosen by the present applicant. In this case, these terms are defined in detail below. Accordingly, the specific terms used herein should be understood based on the unique meanings thereof and the whole context of the present disclosure.

Unless the context dictates otherwise, the word "comprise" or variations such as "comprises" or "comprising" is understood to mean "includes, but is not limited to" such that other elements that are not explicitly mentioned may also be included. The term "unit" herein means a software component or hardware components such as a field-programmable gate array (FPGA) or an application-specific integrated circuit (ASIC), and performs a specific function. However, the term "unit" is not limited to software or hardware. The "unit" may be formed so as to be in an addressable storage medium, or may be formed so as to operate one or more processors. Thus, for example, the term "unit" may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and "units" may be associated with the smaller number of components and "units", or may be divided into additional components and "units".

The term "image" used herein may refer to multi-dimensional data including discrete image elements (for example, pixels for two-dimensional (2D) images and voxels for three-dimensional (3D) images). For example, an image may include a medical image of an object collected by using an X-ray system, a computed tomography (CT) system, a magnetic resonance imaging (MRI) system, an ultrasonic system, or any other medical imaging system.

Also, the term "object' used herein may denote a human being, an animal, or a body part of a human being or an animal. For example, an object may be an organ such as the liver, heart, womb, brain, breast, or stomach, or a blood vessel. Also, the "object" may also be a phantom made of a material having a volume very similar to an effective atomic number and a density of a living creature and having properties similar to those of a human body.

Also, the term "user' used herein may refer to, but is not limited to, a medical expert such as a doctor, a nurse, a clinical pathologist, a medical image expert, a radiologist, or an engineer repairing a medical device.

Hereinafter, exemplary embodiments will be described in detail. However, the present disclosure is not limited to the exemplary embodiments disclosed below, but may be implemented in various forms. The following exemplary embodiments are described to enable those of ordinary skill in the art to embody and practice the invention. Also, parts in the drawings unrelated to the detailed description are omitted to ensure clarity of the present disclosure. Like reference numerals in the drawings denote like elements.

Expressions such as "at least one of," when preceding a list of elements, modify the entire list of elements and do not modify the individual elements of the list.

FIG. 1 is a view for explaining general technologies and content related to exemplary embodiments.

In a medical diagnostic system 30 (see FIG. 2) such as a magnetic resonance imaging (MRI) system, a computed tomography (CT) system, or an X-ray system, a user 5 located in a console room diagnoses an object 10 located in a shield room. The console room and the shield room are separated from each other by a shield wall to protect the user 5 from a magnetic field, radiation, or a radio frequency (RF) signal transmitted from the shield room.

However, the user 5 of the medical diagnostic system 30 needs to observe an inner area of the shield room and the object 10 when diagnosing the object 10. That is, the user 5 needs to directly check various conditions related to the object 10 in the shield room such as a position of the object 10 on a diagnostic table or a movement of the object 10. Accordingly, the shield wall that separates the console room and the shield room may include a console room window 140.

By using the console room window 140, the user 5 who is located in the console room may observe the shield room. The user 5 may diagnose the object 10 while observing the object 10 and the inner area of the shield room through the console room window 140 that is transparent or semitransparent.

As shown in FIG. 1, the user 5 may use a plurality of user interfaces to diagnose the object 10. The user 5 may diagnose the object 10 by controlling a diagnosis process and obtaining a medical image by using a plurality of input units and output units that are connected to the medical diagnostic system 30.

Figure 2:
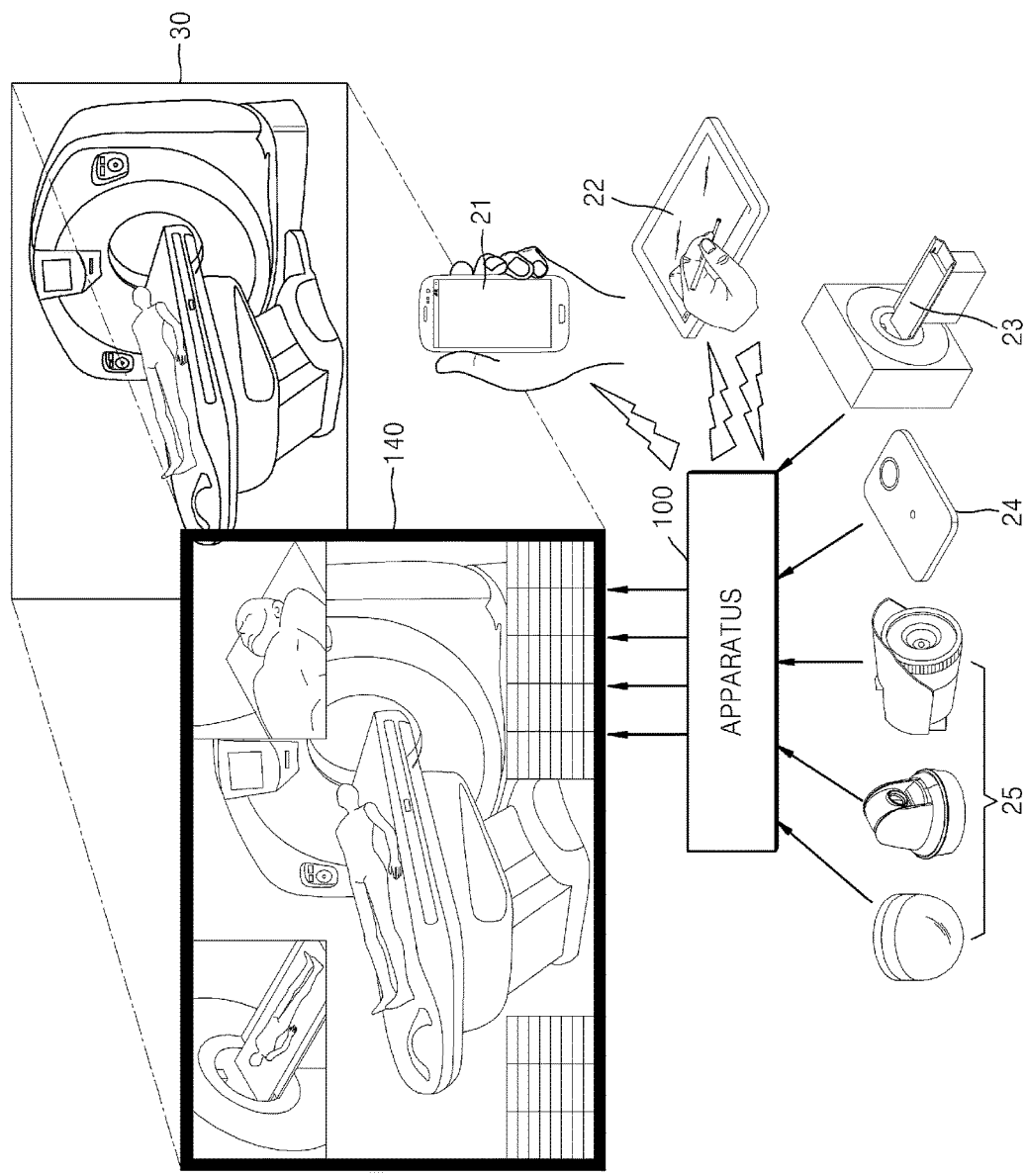
FIG. 2 is a view for explaining a relationship between a medical diagnostic system, a console room window, and an apparatus for providing medical information according to an exemplary embodiment.

FIG. 2 is a view for explaining a relationship between an apparatus 100 for providing medical information, the console room window 140, and the medical diagnostic system 30, according to an exemplary embodiment.

As described above with reference to FIG. 1, the user 5 located in the console room may operate or observe the medical diagnostic system 30 while observing the object 10 in the shield room through the console room window 140.

The apparatus 100 of FIG. 2 may obtain diagnostic information related to the object 10 diagnosed by the medical diagnostic system 30, and may display the obtained diagnostic information on the console room window 140. That is, the apparatus 100 may output diagnostic information by using the console room window 140 instead of a plurality of user interfaces.

The term "diagnostic information" may refer to information which may be used when the object 10 is diagnosed, and may include various types of information obtained by the medical diagnostic system 30 in relation to the object 10. For example, the diagnostic information may include information that is previously stored in relation to the object 10, for example, identification information for identifying the object 10 such as a hospital identification (ID) of a patient, patient information such as an age, a name, or a gender of the object 10, information about a previous imaging test history of the object 10, and information about a list of patients scheduled with an imaging test.

In addition, the diagnostic information may include information about a movement path of the diagnostic table on which the object 10 is placed, a medical image that is obtained by diagnosing the object 10, bio information obtained by photographing a predetermined part of the object 10, an image obtained by photographing an inside of a gantry of the medical diagnostic system 30, an image about a spreading pattern of a contrast agent injected into the object 10, and information about a state of progress of a protocol for diagnosing the object 10.

The diagnostic information is not limited thereto, and may include any general information related to diagnosis of the object 10. Various pieces of diagnostic information will be explained below in detail with reference to FIGS. 20 through 31.

The apparatus 100 may communicate with an external device (not shown) or an external server (not shown) via a network. That is, the apparatus 100 may receive or transmit the diagnostic information by communicating data with the external device or the external server.

In detail, the apparatus 100 may transmit or receive the diagnostic information to or from, for example, a mobile terminal 21 or a computing device 22 that is portable. Also, the apparatus 100 may obtain the diagnostic information generated from a medical device 23 other than the medical diagnostic system 30.

The apparatus 100 may obtain as the diagnostic information an image captured by using a plurality of photographing units 25, and may transmit and receive the diagnostic information through a hospital server 24 such as a picture archiving and communication system (PACS) server.

The apparatus 100 may display the diagnostic information obtained through various methods on the console room window 140. Accordingly, the user 5 of the apparatus 100 may simultaneously observe the inner area of the shield room through the console room window 140 and receive various pieces of information from the apparatus 100 through the console room window 140. That is, the user 5 may observe and diagnose the object 10 at the same time by using information displayed on the console room window 140.

Figure 3:
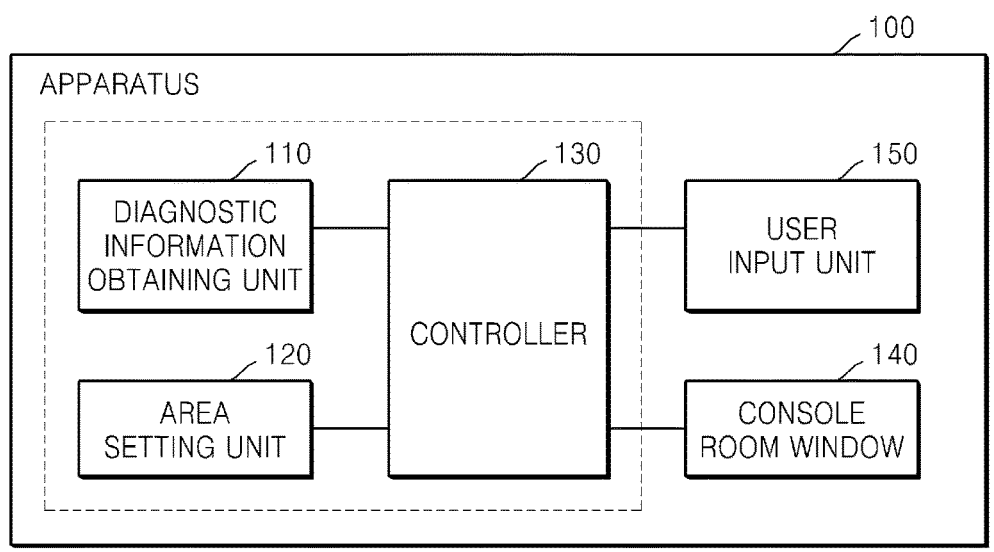
FIG. 3 is a block diagram illustrating an apparatus for providing medical information according to an exemplary embodiment.

FIG. 3 is a block diagram illustrating the apparatus 100 according to an exemplary embodiment. The apparatus 100 may include a diagnostic information obtaining unit 110, an area setting unit 120, a controller 130, the console room window 140, and a user input unit 150. However, elements shown in FIG. 3 are not essential elements of the apparatus 100, and therefore, the above elements may be omitted, modified, or substituted. Also, although it is shown in FIG. 3 that the diagnostic information obtaining unit 110, the area setting unit 120, the controller 130, the console room window 140, and the user input unit 150 are separate elements, it should be noted that two or more of the above elements may be integrated together. For example, the area setting unit 120 may be integrated into the controller 130 such that the controller 130 performs functions of the area setting unit 120.

The apparatus 100 may include more or less elements than those shown in FIG. 3. In an exemplary embodiment, the apparatus 100 may include may include only the diagnostic information obtaining unit 110, the area setting unit 120, and the controller 130. The above elements will now be explained in more detail.

The diagnostic information obtaining unit 110 obtains diagnostic information related to the object 10. As described above with reference to FIG. 2, the diagnostic information may include various types of information which are used when the object 10 is diagnosed.

The diagnostic information obtaining unit 110 may obtain the diagnostic information from the medical diagnostic system 30, an external device, or an external server. For example, the diagnostic information obtaining unit 110 may obtain as the diagnostic information a medical image that is obtained by diagnosing the object 10 from the medical diagnostic system 30. Also, the diagnostic information obtaining unit 110 may obtain the diagnostic information about an imaging test schedule or identification information of a patient from the hospital server 24.

The diagnostic information obtaining unit 110 may communicate with the medical diagnostic system 30, the mobile terminal 21, or the external server by being connected to the medical diagnostic system 30, the mobile terminal, or the external server in a wired or wireless manner, and may obtain the diagnostic information. The diagnostic information obtaining unit 110 may transmit and receive data with any other medical device in a hospital or the hospital server 24 connected through a PACS. Also, the diagnostic information obtaining unit 110 may communicate data according to the digital imaging and communications in medicine (DICOM) standard.

The diagnostic information obtaining unit 110 may include one or more elements that allow communication with an external device, for example a short-range communication module, a wired communication module, and a mobile communication module.

The short-range communication module is a module for short-range communication within a predetermined distance. Examples of a short-range communication technology according to an exemplary embodiment may include, but are not limited to, wireless local area network (LAN), Wi-Fi, Bluetooth, Zigbee, Wi-Fi Direct (WFD), ultra wideband (UWB), infrared data association (IrDA), Bluetooth low energy (BLE), and near field communication (NFC).

The wired communication module is a module for communication using an electrical signal or an optical signal. Examples of a wired communication technology may include a pair cable, a coaxial cable, an optical fiber cable, and an Ethernet cable.

The mobile communication module transmits and/or receives a wireless signal with at least one from among a base station, an external terminal, and a server in a mobile communication network. Examples of the wireless signal may include a voice call signal, a video call signal, and various types of data according to transmission and/or reception of a text or multimedia message.

The area setting unit 120 sets an information providing area on which the diagnostic information is to be displayed on the console room window 140. The term "information providing area" may refer to a portion of or the entire console room window 140 on which the diagnostic information obtained by the diagnostic information obtaining unit 110 is displayed.

The area setting unit 120 may set the information providing area by selecting a size and a position of a predetermined area on the console room window 140. That is, the area setting unit 120 may set the information providing area by determining a position and a size of a rectangular or square area that is previously determined. The information providing area is not limited to a quadrangular shape, and may include various other shapes.

The area setting unit 120 may set the information providing area according to a predetermined standard or a user input that selects the information providing area. For example, the area setting unit 120 may receive a user input that selects a portion or the whole of the console room window 140, and may set the selected area as the information providing area.

Alternatively, the area setting unit 120 may set the information providing area according to various standards such as an importance of the obtained diagnostic information, a detected position of the user 5, and a distance between the user 5 and the console room window 140. For example, the area setting unit 120 may select as the information providing area at least one from among a plurality of sub-areas that are previously set. Also, the area setting unit 120 may select as the information providing area an area corresponding to any one of a plurality of display units constituting the console room window 140 that are arranged adjacent to one another.

The area setting unit 120 may also set an observation area on the console room window 140. The term "observation area" may refer to a portion of or the entire console room window 140 on which the diagnostic information is not displayed. That is, the area setting unit 120 may respectively set the information providing area of the console room window 140 on which the diagnostic information is to be displayed and the observation area of the console room window 140 on which the diagnostic information is not to be displayed.

The area setting unit 120 may set the information providing area from the observation area. That is, when the diagnostic information obtaining unit 110 obtains the diagnostic information, the area setting unit 120 may set as the information providing area a portion or the whole of the observation area of the console room window 140, and may display and output the diagnostic information on the information providing area.

Next, when the display and the output of the diagnostic information is ended, the area setting unit 120 may set the information providing area on which the diagnostic information has been displayed as the observation area. That is, by using the area setting unit 120 which sets the information providing area and the observation area on the console room window 140, the apparatus 100 may efficiently provide the obtained diagnostic information to the user 5.

The controller 130 generally controls elements of the apparatus 100. That is, the controller 130 may control the area setting unit 120 to set the information providing area or the observation area according to the diagnostic information obtained by the diagnostic information obtaining unit 110. Also, the controller 130 may control the console room window 140 to display the diagnostic information on the set information providing area. Furthermore, the controller 130 may control the area setting unit 120 based on a manipulation input of the user 5 received by the user input unit 150.

Thus, the controller 130 may generally control not only the elements of the apparatus 100 but also operations between the elements such as the diagnostic information obtaining unit 110, the area setting unit 120, the console room window 140, and the user input unit 150 included in the apparatus 100.

The console room window 140 displays and outputs the diagnostic information obtained by the diagnostic information obtaining unit 110. The console room window 140 may display and output various types of diagnostic information such as, for example, a medical image, bio information, a control menu, an image obtained by photographing the inside of the shield room, and patient information.

As described above, the console room window 140 may display and output the diagnostic information according to the information providing area and the observation area set by the area setting unit 120. That is, the console room window 140 may display and output the diagnostic information on the information providing area that is a portion or the whole of the console room window 140. Also, the console room window 140 may not display diagnostic information on the observation area that is a portion or the whole of the console room window 140, to allow the user 5 to observe the inside of the shield room.

The console room window 140 may be a transparent or semitransparent member through which the inner area of the shield room may be observed. That is, since the user 5 located in the console room needs to observe the medical diagnostic system 30 and the object 10 in the inner area of the shield room, the console room window 140 may be transparent or semitransparent.

In one embodiment, the console room window 140 may be include at least one from among a projection type transparent display, a direct viewing type transparent display, and a transmissive type transparent display. Also, the console room window 140 may include at least one from among a liquid crystal display (LCD) unit, an organic light-emitting diode (OLED), and a thin film electroluminescent (TFEL) unit.

In addition, the console room window 140 may include a transparent conductive material through which light may be transmitted. The transparent conductive material may comprise at least one from among indium tin oxide (ITO), indium zinc oxide (IZO), zinc oxide (ZnO), indium oxide (In2O3), indium gallium oxide (IGO), and aluminum zinc oxide (AZO).

In one embodiment, the console room window 140 may include a plurality of display units. That is, the console room window 140 may be only one display unit, or alternatively, may include a plurality of display units that are arranged adjacent to one another. When the console room window 140 includes a plurality of display units, a plurality of areas respectively corresponding to the plurality of display units may form the entire console room window 140.

Also, the console room window 140 may include a plurality of preset areas. The plurality of preset areas of the console room window 140 may be determined independently of the display units. The area setting unit 120 may set one or more of the plurality of sub-areas as the information providing area or the observation area.

The console room window 140 will be explained later in detail with reference to FIGS. 11 through 13.

The user input unit 150 may be used by the user 5 to input data to control the apparatus 100. Examples of the user input unit 150 may include, but are not limited to, a keyboard, a mouse, a keypad, a dome switch, a touchpad (e.g., a capacitive overlay type, a resistive overlay type, an infrared type, a surface acoustic wave type, an integral strain gauge type, or a piezoelectric type), a jog wheel, and a jog switch. When a touchpad and a display panel of the console room window 140 have a layered structure, the console room window 140 may be referred to as a touchscreen.

The user input unit 150 may detect a proximity touch as well as a physical touch. The user input unit 150 may detect a touch input (for example, touch and hold, tap, double tap, or click) of medical information. Also, the user input unit 150 may detect a drag gesture from a point at which a touch input is detected. The user input unit 150 may detect a multi-touch input (for example, pinch) of medical information at least one or more positions thereon.

Figure 4:
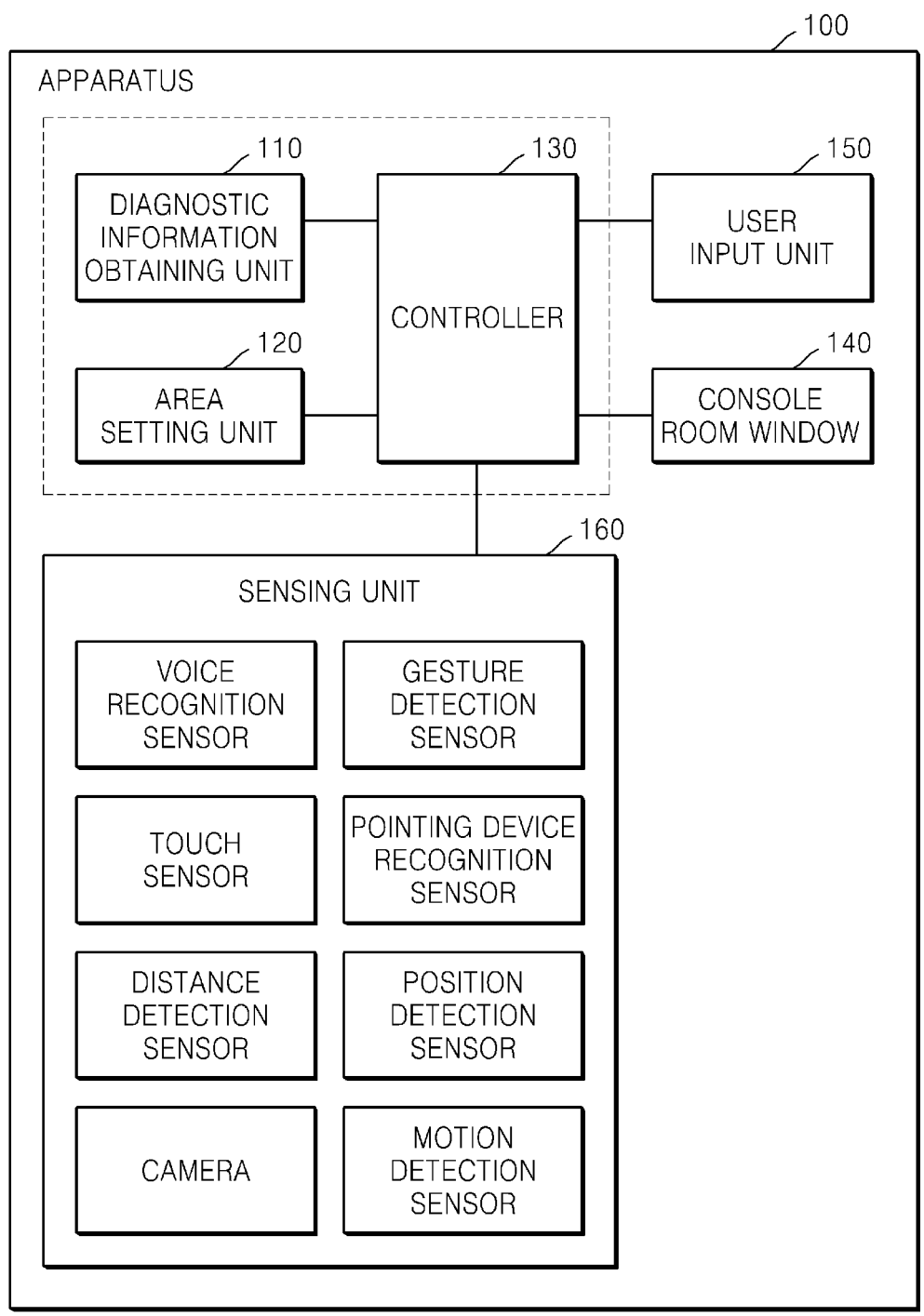
FIG. 4 is a block diagram illustrating an apparatus for providing medical information according to another exemplary embodiment.

FIG. 4 is a block diagram illustrating the apparatus 100 according to another exemplary embodiment. In FIG. 4, descriptions of elements similar or the same as those of FIG. 3 will not be given.

As shown in FIG. 4, the apparatus 100 may further include a sensing unit 160.

The sensing unit 160 may detect the user 5 of the apparatus 100. That is, the sensing unit 160 may detect the user 5, or a state of the user 5 such as a position of the user 5 and a distance between the user 5 and the console room window 140, or an operation by the user 5 such as a touch input of the user 5. To this end, the sensing unit 160 may include various types of sensors.

Also, the sensing unit 160 may detect various targets other than the user 5. For example, the sensing unit 160 may detect whether the object 10 located in the medical diagnostic system 30 moves during diagnosis. In one embodiment, the sensing unit 160 may include various types of sensors such as a speed sensor, a tilt sensor, and a pressure sensor for measuring an amount of movement of the object 10.

Also, the sensing unit 160 may include a photographing unit that photographs the inner area of the shield room. In one embodiment, the photographing unit may include one or more cameras. The photographing unit may photograph various targets located in the shield room such as a diagnostic table on which a patient is placed, a part of the patient to be diagnosed, and an inner area and/or outside area of the gantry. The sensing unit 160 may include various types of photographing units such as, for example, a wide viewing angle camera, a high speed camera, and an infrared camera.

In FIG. 4, the sensing unit 160 may include various types of sensors such as a voice recognition sensor, a gesture detection sensor, a touch sensor, a pointing device recognition sensor, a distance detection sensor, a position detection sensor, a camera, and a motion detection sensor. In addition to the elements shown in FIG. 4, the sensing unit 160 may include various types of sensors for visually, audibly, and dynamically detecting the user 5 and the targets.

FIGS. 5 through 10 are flowcharts illustrating methods of providing medical information, according to various exemplary embodiments. The methods of FIGS. 5 through 10 may include operations performed by the diagnostic information obtaining unit 110, the area setting unit 120, the controller 130, the console room window 140, the user input unit 150, and the sensing unit 160 of the apparatus 100 shown in FIGS. 3 and 4. Accordingly, it will be understood that the descriptions made with respect to FIGS. 2 through 4 may apply to the methods of FIGS. 5 through 10.

Figure 5:
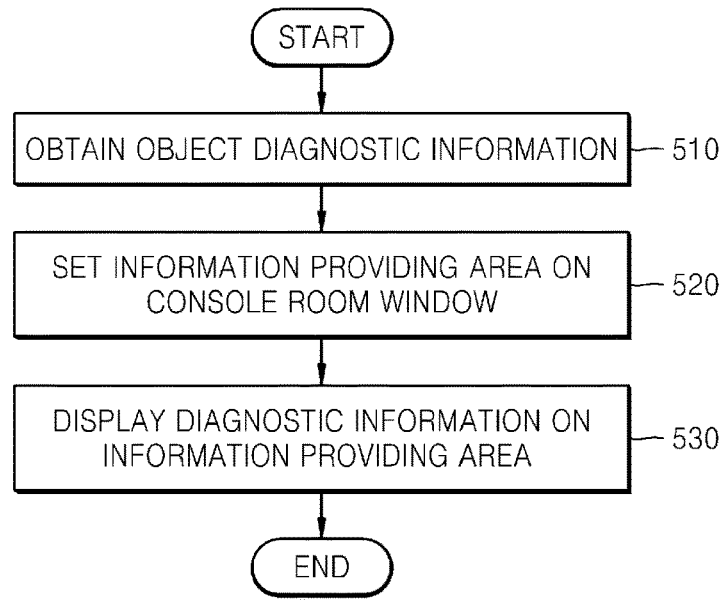
FIG. 5 is a flowchart illustrating a method of providing medical information, according to an exemplary embodiment.

FIG. 5 is a flowchart illustrating a method of providing medical information, according to an exemplary embodiment.

In operation 510, the apparatus 100 obtains diagnostic information of the object 10. As already explained with reference to FIG. 2, the diagnostic information is used when the object 10 is diagnosed and may refer to various types of information obtained by using at least one from among the medical diagnostic system 30, an external device, and an external server.

The apparatus 100 may obtain the diagnostic information generated when diagnosis is initiated and performed on the object 10. That is, the apparatus 100 may obtain new diagnostic information whenever diagnosis is performed on the object 10.

In operation S520, the apparatus 100 sets an information providing area on the console room window 140. That is, the apparatus 100 may set a portion or the whole of the console room window 140 as the information providing area. As described above with reference to FIG. 2, the information providing area may refer to an area on which the diagnostic information is to be displayed.

In detail, the apparatus 100 may set the information providing area on which the diagnostic information is to be displayed based on at least one from among a type of the diagnostic information obtained in operation 510, a size of an area occupied by the diagnostic information on the console room window 140, an importance of the diagnostic information, and priorities of a plurality of sub-areas on the console room window 140.

In one embodiment, the apparatus 100 may set as the information providing area at least one from among the plurality of sub-areas that are preset in operation 520, which will be explained later in detail with reference to FIG. 12.

Also, when the console room window 140 includes a plurality of transparent display units that are arranged adjacent to one another, the apparatus 100 may determine as the information providing area an area corresponding to at least one from among the plurality of transparent display units, which will be explained later in detail with reference to FIG. 13.

Alternatively, when a user input is received, the apparatus 100 may set the information providing area based on the user input, which will be explained later in detail with reference to FIGS. 8, 11, and 12.

In operation 530, the apparatus 100 displays the diagnostic information on the information providing area. That is, the apparatus 100 may provide the diagnostic information obtained in operation 510 on the information providing area set in operation 520.

When the apparatus 100 displays the diagnostic information on the console room window 140 that is a transparent display unit in operation 530, the user 5 may simultaneously observe the inner area of the shield room and check the diagnostic information. That is, since the diagnostic information is displayed on the console room window 140 instead of a plurality of interface units, the user 5 may simultaneously check a condition of the inner area of the shield room and the diagnostic information, thereby substantially minimizing a need for shifting a viewing direction of the user 5.

The descriptions made with reference to FIG. 5 may apply to a plurality of pieces of diagnostic information. That is, the apparatus 100 may obtain a plurality of pieces of diagnostic information in operation 510, may set a plurality of information providing areas in operation 520, and respectively display the plurality of pieces of diagnostic information on the plurality of information providing areas in operation 530.

The plurality of pieces of diagnostic information may be respectively matched to the plurality of information providing areas, and the apparatus 100 may respectively output the plurality of pieces of diagnostic information to the matched information providing areas to be displayed.

Figure 6:
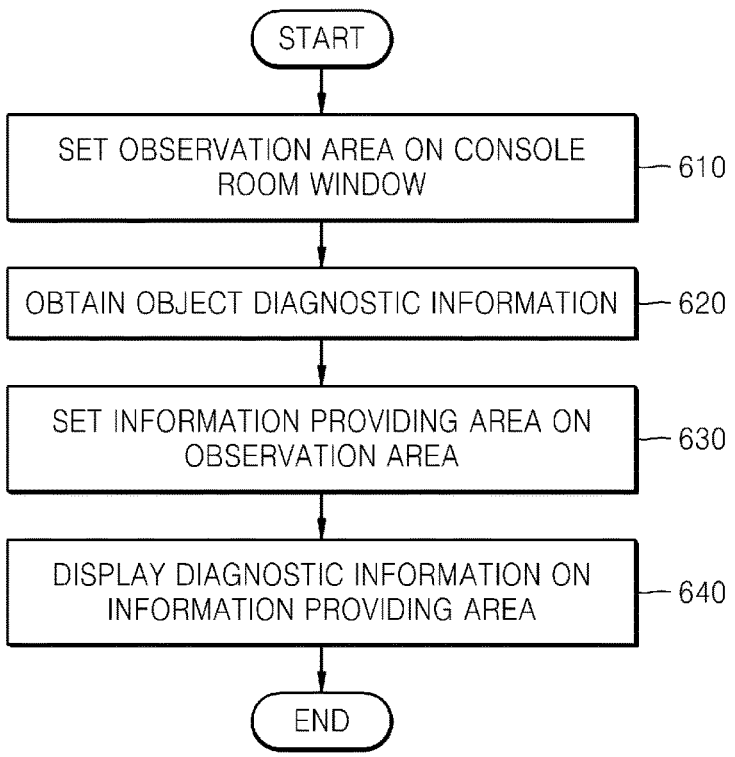
FIG. 6 is a flowchart illustrating a method of providing medical information, according to another exemplary embodiment.

FIG. 6 is a flowchart illustrating a method of providing medical information, according to another exemplary embodiment.

In operation 610, the apparatus 100 sets an observation area on the console room window 140. As described above with reference to FIG. 2, the observation area may refer to an area on which diagnostic information is not displayed to allow observation of the inside of the shield room.

That is, in operation 610, the apparatus 100 sets a portion of or all of the console room window 140 as the observation area. When diagnostic information is obtained before operation 610, the apparatus 100 may determine as the observation area an area other than an area of the console room window 140 on which the diagnostic information is displayed. On the other hand, when no diagnostic information is obtained before operation 610, the apparatus 100 may determine the whole of the console room window 140 as the observation area.

In operation 620, the apparatus 100 obtains the diagnostic information. Operation 620 is similar to operation 510, and thus a detailed explanation thereof will not be given.

In operation 630, the apparatus 100 sets an information providing area on the observation area. That is, the apparatus 100 may set as the information providing area a portion or the whole of the observation area set in operation 610.

In detail, the apparatus 100 may determine an area on which the obtained diagnostic information is to be displayed in the observation area on which the diagnostic information is not currently displayed on the console room window 140. That is, the apparatus 100 may select a portion or the whole of an empty area on the console room window 140 as the information providing area in consideration of, for example, a type of the diagnostic information obtained in operation 620, a size of an area occupied by the diagnostic information, and priorities of sub-areas included in the console room window 140.

In operation 640, the apparatus 100 displays the diagnostic information on the information providing area. The apparatus 100 may display the diagnostic information obtained in operation 620 on the information providing area set in operation 630.

Alternatively, the apparatus 100 may set the information providing area irrespective of the observation area, which is different from the embodiment of FIG. 6. In detail, when the observation area of the console room window 140 is not sufficient in size for an area required to display the diagnostic information obtained in operation 620, the apparatus 100 may set a portion of an area on which the diagnostic information has already been displayed and a portion of the observation area as the information providing area.

That is, when a plurality of pieces of diagnostic information are displayed on the console room window 140 and the observation area is not sufficient for an area on which new diagnostic information is to be displayed, the apparatus 100 may display the new diagnostic information such that the new diagnostic information overlaps with the diagnostic information that has already been displayed on the console room window 140. That is, the apparatus 100 may set a portion or the whole of an area on which the diagnostic information that has been already been displayed and a portion or the whole of the observation area as an information providing area for the new diagnostic information.

Figure 7:
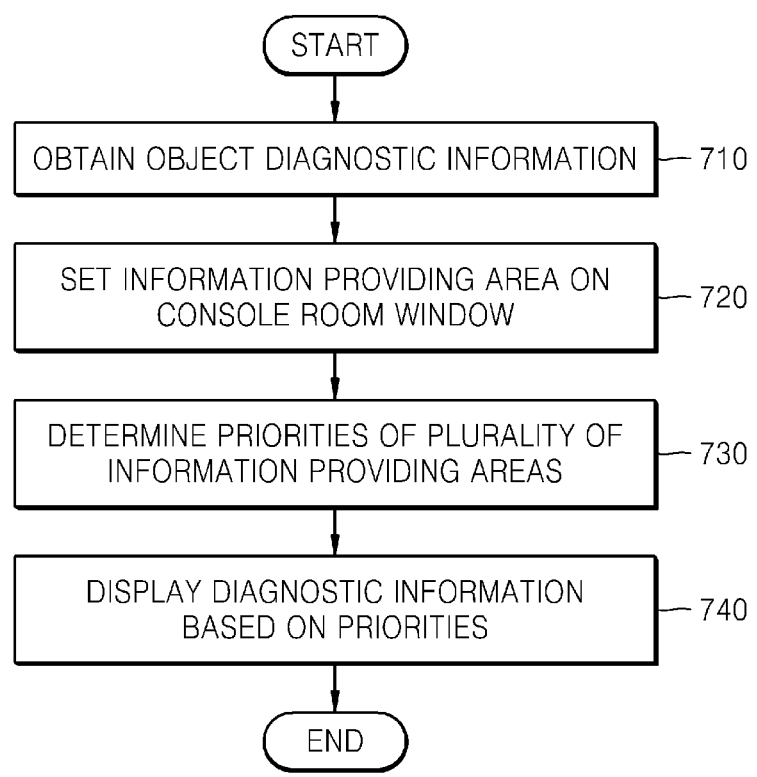
FIG. 7 is a flowchart illustrating a method of outputting diagnostic information according to priorities of a plurality of information providing areas, according to an exemplary embodiment.

FIG. 7 is a flowchart illustrating a method of outputting diagnostic information according to priorities of a plurality of information providing areas, according to an exemplary embodiment.

In operation 710, the apparatus 100 obtains diagnostic information of the object 10. In operation 710, the apparatus 100 may obtain a plurality of pieces of diagnostic information, similar to operation 510 of FIG. 5.

In operation 720, the apparatus 100 sets a plurality of information providing areas on the console room window 140. That is, the apparatus 100 may set the plurality of information providing areas on the console room window 140 to display the plurality of pieces of diagnostic information obtained in operation 710.

The apparatus 100 may set the plurality of information providing areas such that the plurality of information providing areas do not overlap with one another or some or all of the plurality of information providing areas overlap with one another.

In operation 730, the apparatus 100 determines priorities of the plurality of information providing areas. That is, the apparatus 100 may determine priorities of the plurality of information providing areas set in operation 720 to determine orders in which the plurality of pieces of diagnostic information are to be displayed.

The apparatus 100 may receive a user input that sets the priorities of the plurality of information providing areas, and may determine the priorities according to the user input. Alternatively, the apparatus 100 may determine the priorities of the plurality of information providing areas in consideration of, for example, at least one from among positions of the plurality of information providing areas and a positional relationship between the user 5 and the information providing areas.

In operation 740, the apparatus 100 displays the diagnostic information based on the determined priorities of the plurality of information providing areas. In one embodiment, the apparatus 100 may determine in which orders and at which positions the plurality of pieces of diagnostic information are to be displayed, in consideration of orders in which the plurality of pieces of diagnostic information are obtained and the determined priorities of the plurality of information providing areas.

For example, the apparatus 100 may detect a position of the user 5 by using the sensing unit 160, and may assign a higher priority to an information providing area positioned closer to the user 5. Next, the apparatus 100 may match diagnostic information that is obtained earlier to an information providing area having a higher priority.

The apparatus 100 may display and output the plurality of pieces of diagnostic information to the matched information providing areas, which will be explained later in more detail with reference to FIG. 14.

Although not shown in FIG. 7, in an alternative embodiment, the apparatus 100 may output a plurality of pieces of diagnostic information in consideration of importances of the plurality of pieces of diagnostic information. That is, the apparatus 100 may obtain a plurality of pieces of diagnostic information, and may determine importances according to types of the plurality of pieces of diagnostic information. Here, the importances of the plurality of pieces of diagnostic information may be determined in advance and identified by the apparatus 100.

Next, the apparatus 100 may sequentially match diagnostic information having a higher importance to an information providing area having a higher priority. The apparatus 100 may respectively display and output the plurality of pieces of diagnostic information to the matched information providing areas, which will be explained later in more detail with reference to FIG. 15.

Figure 8:
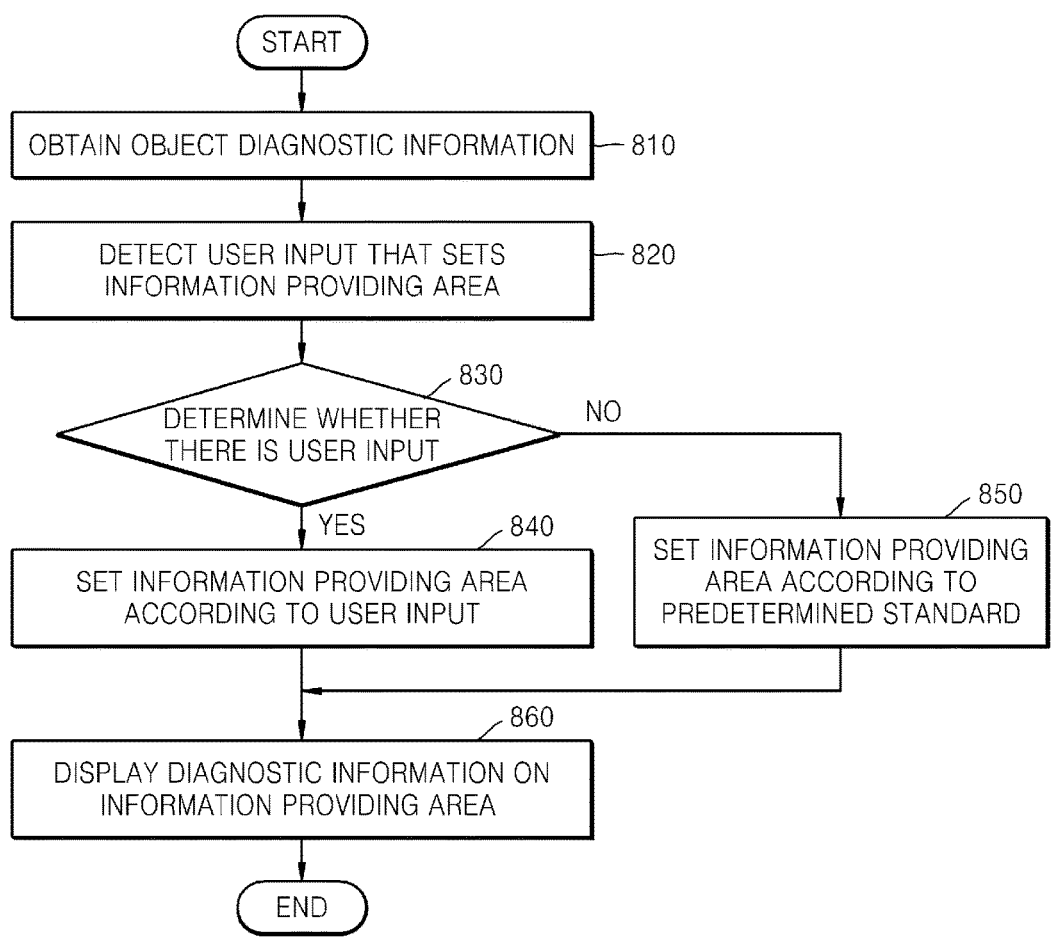
FIG. 8 is a flowchart illustrating a method of outputting diagnostic information according to a user input, according to an exemplary embodiment.

FIG. 8 is a flowchart illustrating a method of outputting diagnostic information according to a user input, according to an exemplary embodiment.

In operation 810, the apparatus 100 obtains diagnostic information of the object 10, similar to operation 510 of FIG. 5.

In operation 820, the apparatus 100 detects a user input that sets an information providing area. That is, the apparatus 100 may detect a user input that is received through the user input unit 150. Examples of the user input may include an input using, for example, an input unit such as a touch panel, a keypad, or a mouse, and an input that directly touches the console room window 140.

In operation 830, it is determined whether a user input exists. When it is determined in operation 830 that a user input exists, the method proceeds to operation 840. When it is determined in operation 830 that no user input exists, the method proceeds to operation 850.

In operation 840, the apparatus 100 may set the information providing area according to the user input. In one embodiment, the apparatus 100 may detect a user input that determines an information providing area having a predetermined shape and a predetermined size at a predetermined position on the console room window 140, and may set the information providing area according to the predetermined shape, the predetermined position, and the predetermined size determined by the user input.

Thus, the apparatus 100 may set the information providing area such that the diagnostic information obtained in operation 810 is to be output and displayed to have the predetermined size and the predetermined position on the console room window 140 according to the user input.

In operation 860, the apparatus 100 outputs the diagnostic information to be displayed on the information providing area determined by the user 5.

In operation 850, the apparatus 100 may set the information providing area according to a predetermined standard. In one embodiment, the apparatus 100 may set a portion or the whole of an observation area as the information providing area as described above with reference to FIGS. 5 through 7. Alternatively, the apparatus 100 may set the information providing area in consideration of an importance of the diagnostic information or preset priorities of sub-areas of the console room window 140.

In operation 860, the apparatus 100 outputs the diagnostic information to be displayed on the information providing area set in operation 850.

Figure 9:
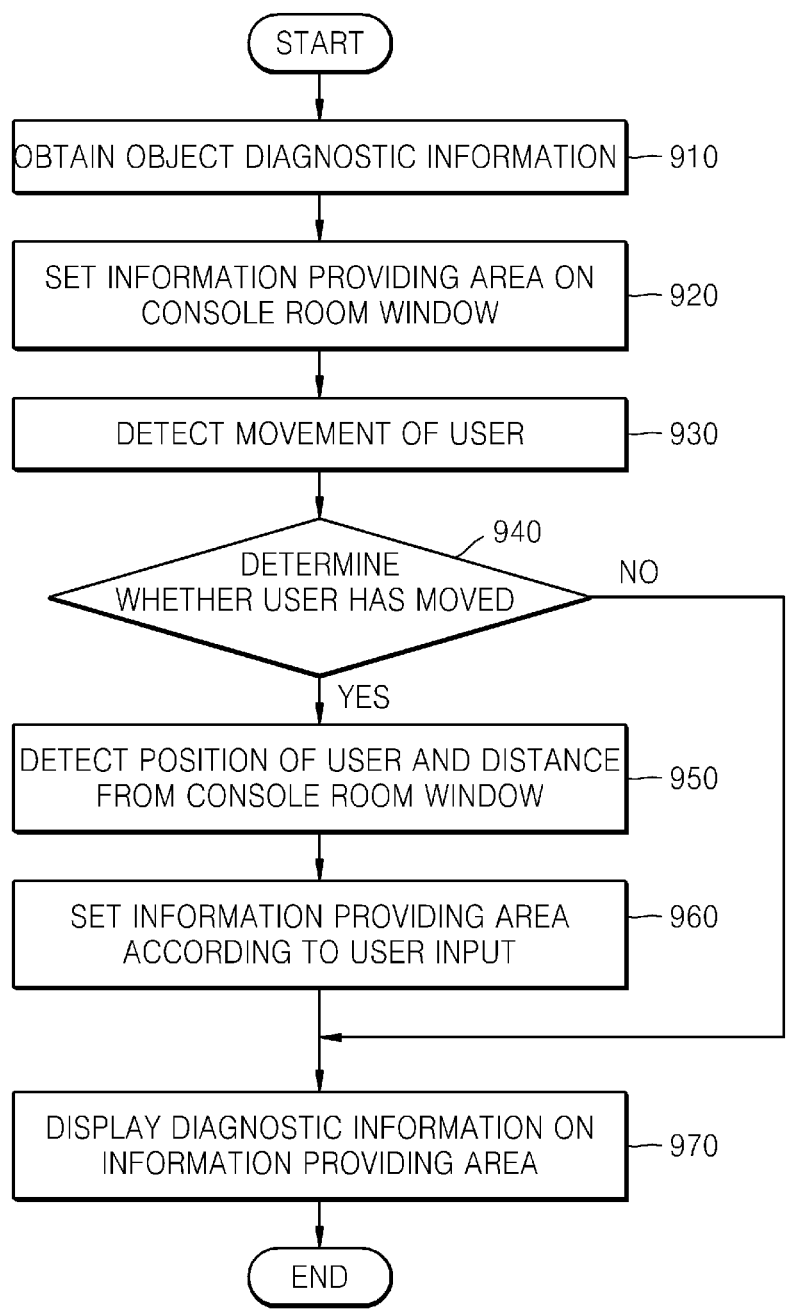
FIG. 9 is a flowchart illustrating a method of detecting a user and outputting diagnostic information, according to an exemplary embodiment.

FIG. 9 is a flowchart illustrating a method of detecting the user 5 and outputting information, according to an exemplary embodiment.

In operation 910, the apparatus 100 obtains diagnostic information of the object 10, similar to operation 510 of FIG. 5.

In operation 920, the apparatus 100 sets an information providing area on the console room window 140. The apparatus 100 may set the information providing area according to various conditions and standards, and various exemplary embodiments of setting the information providing area described with reference to FIGS. 5 through 8 may apply.

In operation 930, the apparatus 100 detects a movement of the user 5. In one embodiment, the apparatus 100 may detect the movement of the user 5 by using various sensors such as a gesture detection sensor and a pointing device recognition sensor included in the sensing unit 160.

In operation 940, it is determined whether the movement of the user 5 is detected. When it is determined in operation 940 that a movement of the user 5 is detected, the method proceeds to operation 950. When it is determined in operation 940 that a movement of the user 5 is not detected, the method proceeds to operation 970.

In operation 950, the apparatus 100 detects a position of the user 5, and a distance between the user 5 and the console room window 140. In one embodiment, the apparatus 100 may detect a position of the user 5, and a distance between the user 5 and the console room window 140, by using sensors such as a depth sensor, a distance sensor, a position sensor, and a gesture detection sensor.

The position of the user 5 may refer to two-dimensional (2D) or three-dimensional (3D) coordinates of the user 5 that may be determined based on a center or a predetermined point of the console room window 140. The distance between the user 5 and the console room window 140 may be a shortest distance between the detected user 5 and the center or the predetermined point of the console room window 140.

In operation 960, the apparatus 100 adjusts the information providing area based on the position of the user 5 and the distance which are detected in operation 950. That is, the apparatus 100 may adjust the information providing area set in operation 920.

For example, the apparatus 100 may adjust a size of the information providing area based on the distance between the user 5 and the console room window 140. That is, the apparatus 100 may increase a size of the information providing area when the user 5 is farther away from the console room window 140. Accordingly, the apparatus 100 may output diagnostic information to be displayed in a larger information providing area. On the other hand, when the user 5 is closer to the console room window 140, the apparatus 100 may reduce a size of the information providing area on which the diagnostic information is displayed.

Also, in one embodiment, the apparatus 100 may adjust a position of the information providing area based on a position of the user 5. For example, when the user 5 is located on a right side from the center of the console room window 140, the apparatus 100 may move the position of the information providing area closer toward the right side of the console room window 140. Thus, according to the exemplary embodiment of FIG. 9, the apparatus 100 may display the diagnostic information at a position closer to the user 5 even when the user 5 moves in the console room.

Further, in one embodiment, the apparatus 100 may adjust a size of the information providing area based on a position of the user 5. For example, when the user 5 is located on a left side from the center of the console room window 140, the apparatus 100 may reduce a size of the information providing area located on the left side from the center of the console room window 140.

Also, when the user 5 is located on a left side from the center of the console room window 140, the apparatus 100 may increase a size of the information providing area located on a right side from the center of the console room window 140. Thus, the apparatus 100 may reduce a size of the information providing area that is closer to the user 5, and may increase a size of the information providing area that is farther away from the user 5.

In one embodiment, the apparatus 100 may determine a priority of the information providing area based on the position of the user 5. That is, when priorities of a plurality of sub-areas on the console room window 140 are preset, the apparatus 100 may change the priorities of the plurality of sub-areas when the user 5 moves.

For example, when the user 5 is located on a right side from the center of the console room window 140, priorities of sub-areas located on the right side from among a plurality of sub-areas of the console room window 140 may be set to be higher. Accordingly, the apparatus 100 may output and display diagnostic information in the sub-areas located on the right side that are closer to the user 5 earlier than in the sub-areas located on the remaining sub-areas.

In operation 970, the apparatus 100 displays the diagnostic information on the information providing area. That is, the apparatus 100 may display the diagnostic information on the information providing area that is set in operation 920 or the information providing area that is adjusted in operation 960.

In FIG. 9, the apparatus 100 may provide diagnostic information having a predetermined size to the user 5 by adjusting a size and a position of an information providing area when at least one from among a position of the user 5 and a distance between the user 5 and the console room window 140 is changed. Also, the apparatus 100 may provide diagnostic information to be displayed closer to the user 5 by setting the information providing area to a position closer to the user 5 on the console room window 140 when the user 5 moves.

Figure 10:
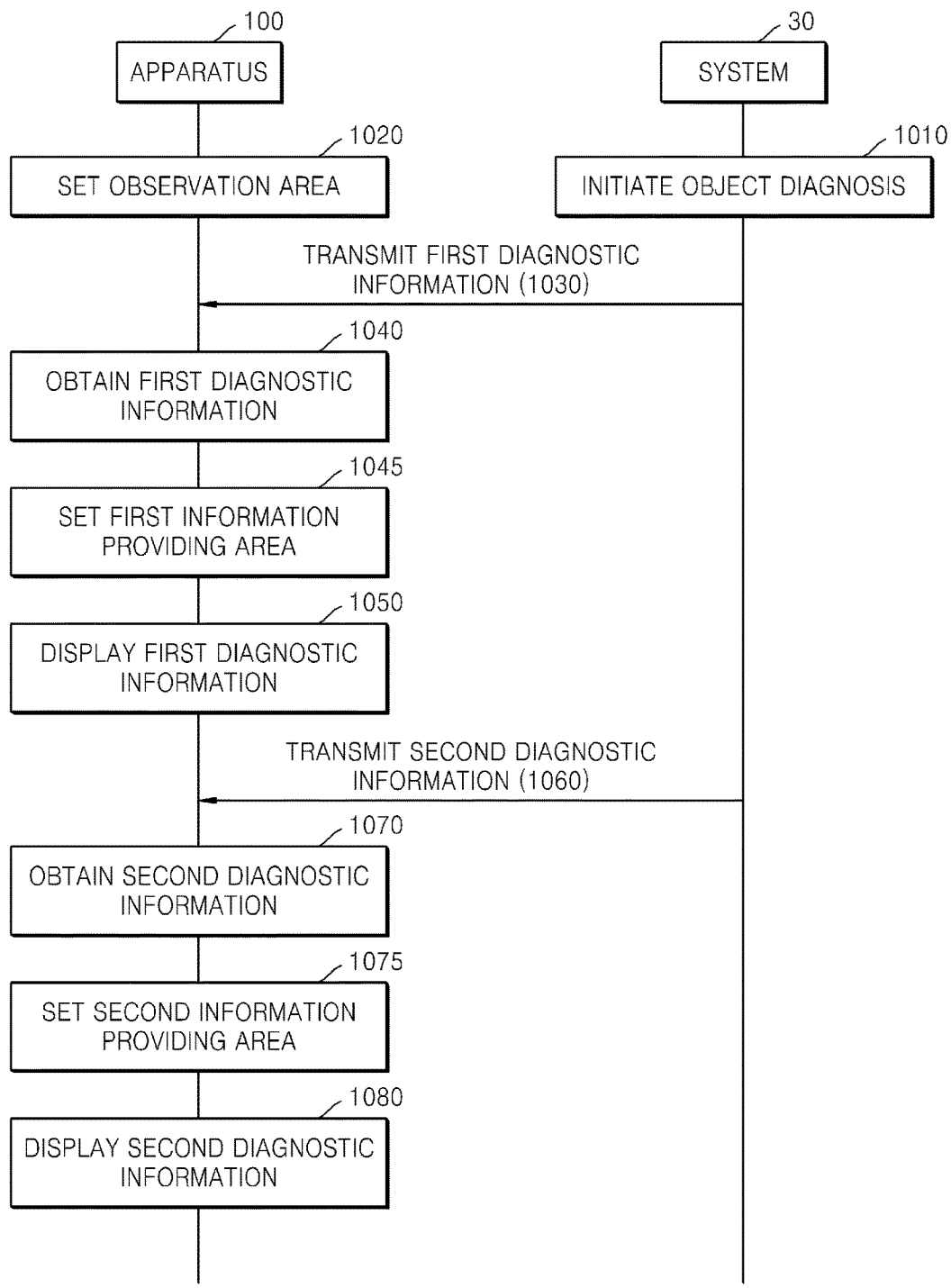
FIG. 10 is a flowchart for explaining an operation between an apparatus for providing medical information and a medical diagnostic system, according to an exemplary embodiment.

FIG. 10 is a flowchart for explaining an operation between the apparatus 100 and the medical diagnostic system 30, according to an exemplary embodiment.

In operation 1010, the medical diagnostic system 30 initiates diagnosis on the object 10. For example, the medical diagnostic system 30 may check patient information of the object 10, and when the object 10 is placed on the diagnostic table, may adjust a position of the diagnostic table. Next, the medical diagnostic system 30 performs the diagnosis by, for example, loading a protocol for examining the object 10. In addition, in operation 1010, the medical diagnostic system 30 may perform various processes related to performing the diagnosis on the object 10, for example, a process of injecting a contrast agent into the object 10.

In operation 1020, the apparatus 100 sets an observation area on the console room window 140. That is, the apparatus 100 may set as the observation area an empty area of the console room window 140 before the diagnostic information is obtained.

In operation 1030, the apparatus 100 receives first diagnostic information from the medical diagnostic system 30. The medical diagnostic system 30 may directly transmit the first diagnostic information to the apparatus 100 as shown in FIG. 10, or may transmit the first diagnostic information through a hospital server or an external server.

In operation 1040, the apparatus 100 obtains the first diagnostic information. Next, the apparatus 100 may check a type of the first diagnostic information, an importance of the first diagnostic information, and a size to be occupied by the first diagnostic information when displayed on the console room window 140.

In operation 1045, the apparatus 100 sets a first information providing area. That is, the apparatus 100 may set the first information providing area matching the first diagnostic information obtained in operation 1040. The apparatus 100 may set and adjust the first information providing area according to various conditions. Here, various exemplary embodiments with reference to FIGS. 5 through 9 may apply.

In operation 1050, the apparatus 100 displays the first diagnostic information. That is, the apparatus 100 may provide the first diagnostic information to the first information providing area matching the first diagnostic information.

In operation 1060, the apparatus 100 receives second diagnostic information. That is, the medical diagnostic system 30 may transmit the second diagnostic information obtained when the object 10 is diagnosed to the apparatus 100. Although only the first and the second diagnostic information is shown in FIG. 10, the medical diagnostic system 30 may generate a plurality of pieces of diagnostic information in addition to the first and the second diagnostic information, and may transmit the plurality of pieces of diagnostic information to the apparatus 100.

In operation 1070, the apparatus 100 obtains the second diagnostic information. Similar to operation 1040, the apparatus 100 may check various pieces of information about the second diagnostic information.

Next, in operation 1075, the apparatus 100 may set and adjust a second information providing area, and in operation 1080, the apparatus 100 may display the second diagnostic information on the set second information providing area.

Although two pieces of diagnostic information, the first and the second diagnostic information, are shown in FIG. 10, the above series of processes may be repeatedly performed until the medical diagnostic system 30 terminates performing diagnosis on the object 10 or the apparatus 100 terminates receiving diagnostic information.

Figure 11:
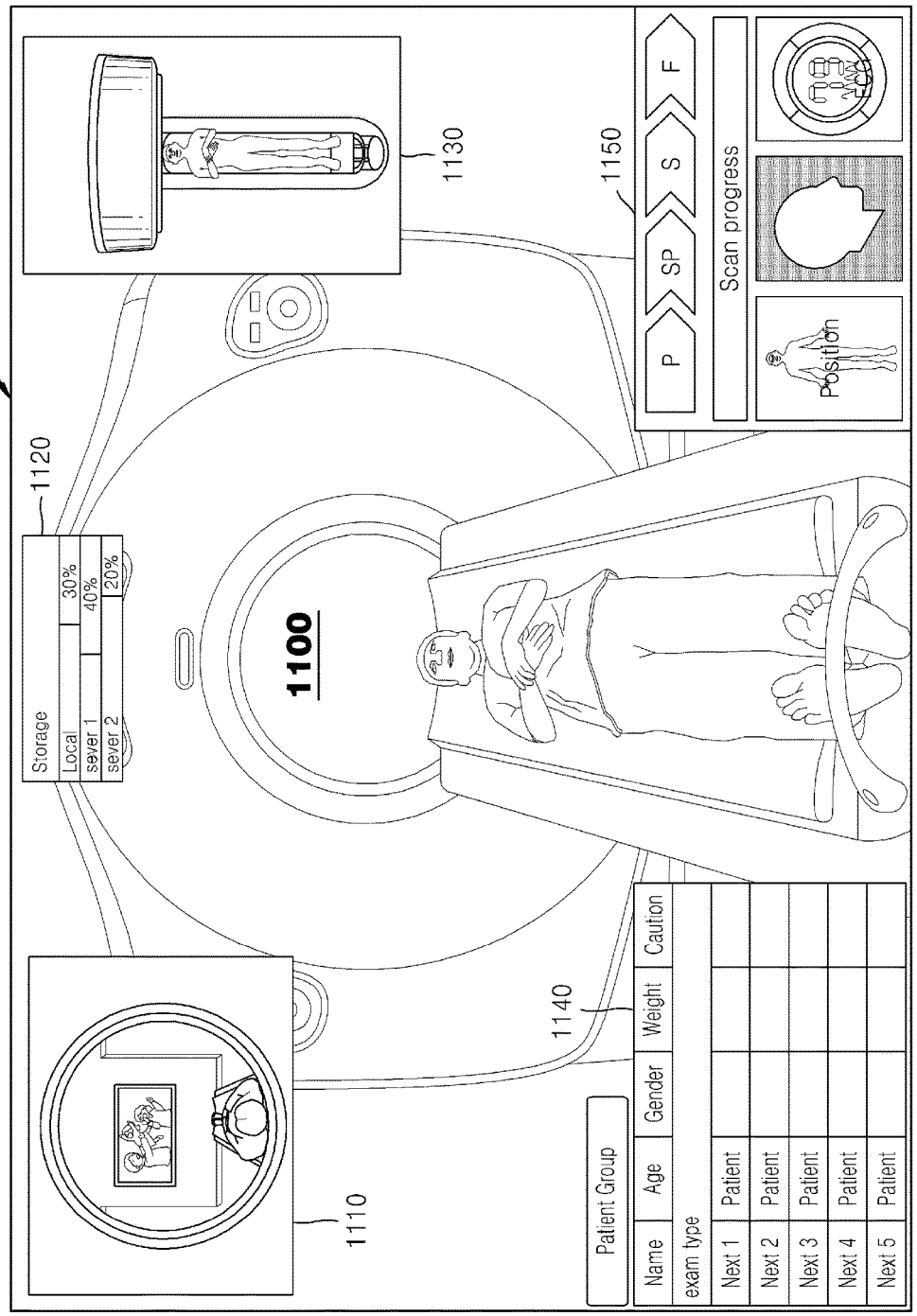
FIG. 11 is a view illustrating various diagnostic information displayed on a console room window, according to an exemplary embodiment.

FIG. 11 is a view illustrating various pieces of diagnostic information displayed on the console room window 140, according to an exemplary embodiment.

The user 5 may observe the medical diagnostic system 30 and the object 10 in the inner area of the shield room through the console room window 140. For example, the console room window 140 may be a transparent display unit. The apparatus 100 displays various types of diagnostic information on the console room window 140. Accordingly, the apparatus 100 may provide to the user 5 a condition of the inner area of the shield room and diagnostic information of the object 10 without distracting attention of the user 5. Also, a need for a space for installing a plurality of user interfaces in the inner area of the console room may be obviated and thus space utilization may be increased.

In FIG. 11, the apparatus 100 obtains an image obtained by photographing the inside of the gantry of the medical diagnostic system 30 as first diagnostic information, and outputs the first diagnostic information to a first area 1110 that is a left upper area of the console room window 140. Next, the apparatus 100 obtains information about a storage space of a local memory of the medical diagnostic system 30 as second diagnostic information, and outputs the second diagnostic information to a second area 1120 that is a center upper area of the console room window 140 on which the first diagnostic information is not displayed.

Also, the apparatus 100 obtains an image obtained by photographing a movement of the diagnostic table on which the object 10 is placed as third diagnostic information, and outputs the third diagnostic information to a third area 1130 that is a right upper area of the console room window 140. Further, the apparatus 100 obtains information about a list of patients to be diagnosed as fourth diagnostic information, and outputs the fourth diagnostic information to a fourth area 1140 that is a left lower area of the console room window 140. Next, the apparatus 100 obtains information about a state of progress of a protocol for diagnosing the object 10 as fifth diagnostic information, and outputs the fifth diagnostic information to a fifth area 1150 that is a right lower area of the console room window 140.

Each piece of first to fifth diagnostic information will now be explained in detail. First, the apparatus 100 may photograph the inner area of the gantry by using a camera located inside the shield room. Next, the apparatus 100 may obtain an image captured by the camera as the first diagnostic information. The user 5 may visually check the object 10 that is moved into the medical diagnostic system 30 by using the first diagnostic information.

The apparatus 100 may obtain information about the local memory as the second diagnostic information to store a generated medical image. The user 5 may determine whether or not there is a sufficient storage space in the local memory of the medical diagnostic system 30 by checking the second diagnostic information. The apparatus 100 may secure the storage space of the medical diagnostic system 30 according to a user input that transmits part of pre-stored data to an external server such as a PACS server.

The apparatus 100 may capture an image of a movement path of the diagnostic table by using a camera disposed on a ceiling of the shield room. That is, the apparatus 100 may photograph the inner area of the shield room by using the camera disposed in the shield room to obtain an image, and may use this image as the third diagnostic information.

The apparatus 100 may obtain information about a list of patients from the PACS server as the fourth diagnostic information. That is, the apparatus 100 may enable the user 5 to manage an imaging test schedule by providing the fourth diagnostic information about the list of the patients.

Finally, the apparatus 100 may obtain information about a protocol for diagnosing the object 10 as the fifth diagnostic information. For example, by using the fifth diagnostic information, the user 5 may determine whether the protocol is in a preparation (P) step, a scan planning (SP) step, a scanning (S) step, or a finishing (F) step. Also, the apparatus 100 may provide information about a posture of the object 10 or electro cardiography (ECG) related to the protocol as the fifth diagnostic information.

As described above, the apparatus 100 may obtain various types of diagnostic information from the medical diagnostic system 30, the PACS server, or a hospital external server. Next, the apparatus 100 may set an information providing area for displaying the obtained diagnostic information on the console room window 140, and may output each piece of diagnostic information to the corresponding information providing area.

The apparatus 100 may set an area of the console room window 140 on which diagnostic information is not currently displayed as an observation area, as described above with reference to FIG. 2. Next, the apparatus 100 may set a portion of the observation area as an information providing area for displaying newly obtained diagnostic information.

For example, in FIG. 11, when sixth diagnostic information that is new diagnostic information is additionally obtained, the apparatus 100 may output the sixth diagnostic information to an area other than the five areas 1110, 1120, 1130, 1140, and 1150 on the console room window 140. However, a size of the area other than the first through fifth areas 1110, 1120, 1130, 1140, and 1150 may not be sufficient to output the sixth diagnostic information. In this case, the apparatus 100 may set an information providing area on which the sixth diagnostic information is to be displayed such that the information providing area partially or entirely overlaps with the first through fifth areas 1110, 1120, 1130, 1140, and 1150.

The apparatus 100 may adjust a position and a size of the information providing area according to the user's selection. Also, the apparatus 100 may adjust the information providing area based on priorities of a plurality of sub-areas included in the console room window 140 or an importance of the diagnostic information. The apparatus 100 may control a position and a size of the diagnostic information displayed on the console room window 140 by adjusting the information providing area.

Also, the apparatus 100 may adjust a transparency of the diagnostic information displayed on the information providing area. That is, the apparatus 100 may adjust a transparency of the diagnostic information displayed on the information providing area to, for example, a transparent level, a semitransparent level, or an opaque level. Based on the transparency of the diagnostic information, the user 5 may observe the inner area of the shield room through the information providing area, may observe both the diagnostic information and the inner area of the shield room, or may observe only the diagnostic information.

The apparatus 100 may adjust a transparency of the diagnostic information based on a preset condition, a value of the diagnostic information, or a user input. For example, the apparatus 100 may adjust a transparency of the diagnostic information based on a type of the diagnostic information. For example, the apparatus 100 may opaquely display diagnostic information about a medical image, and may semitransparently display text-based diagnostic information such as a list of patients.

Also, the apparatus 100 may adjust a transparency of diagnostic information based on a position of the information providing area on which the diagnostic information is displayed. That is, the apparatus 100 may increase a transparency of diagnostic information when the diagnostic information is displayed closer to an outer edge portion of the console room window 140, and may reduce a transparency of diagnostic information when the diagnostic information is displayed closer to a center portion of the console room window 140. Accordingly, the user 5 may check the diagnostic information while easily observing the inner area of the shield room through the center portion of the console room window 140.

Figure 12:
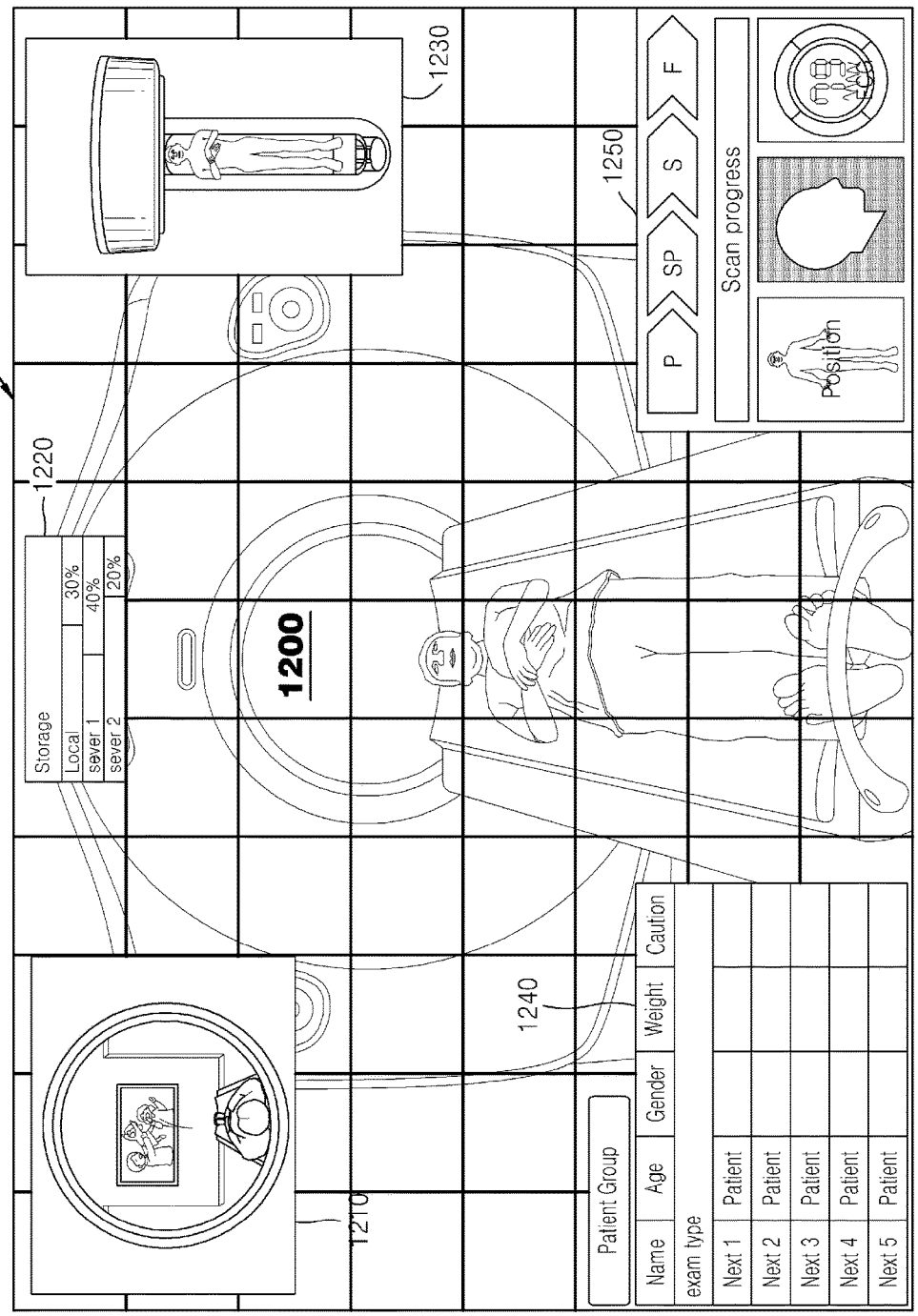
FIG. 12 is a view illustrating a plurality of sub-areas of a console room window, according to an exemplary embodiment.

FIG. 12 is a view illustrating a plurality of sub-areas of the console room window 140, according to an exemplary embodiment.

Referring to FIG. 12, the apparatus 100 may set a plurality of sub-areas constituting the console room window 140. That is, the apparatus 100 may set a plurality of sub-areas by dividing the console room window 140 in a horizontal direction and a vertical direction. The apparatus 100 may set the plurality of sub-areas of a predetermined number. The number and arrangement of the plurality of sub-areas are exemplary, and exemplary embodiments are not limited thereto.

The apparatus 100 may obtain diagnostic information, and may set at least one from among the plurality of sub-areas as an information providing area. The apparatus 100 detects sub-areas corresponding to an observation area on which the diagnostic information is not currently displayed from among the plurality of areas. Next, the apparatus 100 may set at least one from among the sub-areas corresponding to the observation area as an information providing area for the diagnostic information.

The number and shapes of sub-areas selected by the apparatus 100 may vary according to a type of the diagnostic information. For example, the apparatus 100 may select sub-areas whose shapes and numbers vary according to whether the diagnostic information is to be displayed in a horizontal direction or in a vertical direction.

In FIG. 12, the apparatus 100 may select a first area 1210 comprising 3×3 sub-areas to display first diagnostic information about an image of the inside of the gantry on a left upper area of the console room window 140. On the other hand, the apparatus 100 may select a second area 1220 comprising 3×1 sub-areas to display second diagnostic information about the local memory on an upper area of the console room window 140. Also, the apparatus 100 may select a third area 1230 comprising 3×4 sub-areas to display third diagnostic information about an image obtained by photographing a movement of the diagnostic table on a right upper area of the console room window 140, select a fourth area 1240 comprising 4×3 sub-areas to display fourth diagnostic information about a list of patients to be diagnosed on a left lower of the console room window 140, and the apparatus 100 may select a fifth area 1250 comprising 4×3 sub-areas to display fifth diagnostic information about a state of progress of a protocol for diagnosing the object 10 on a right lower area of the console room window 140.

Figure 13:
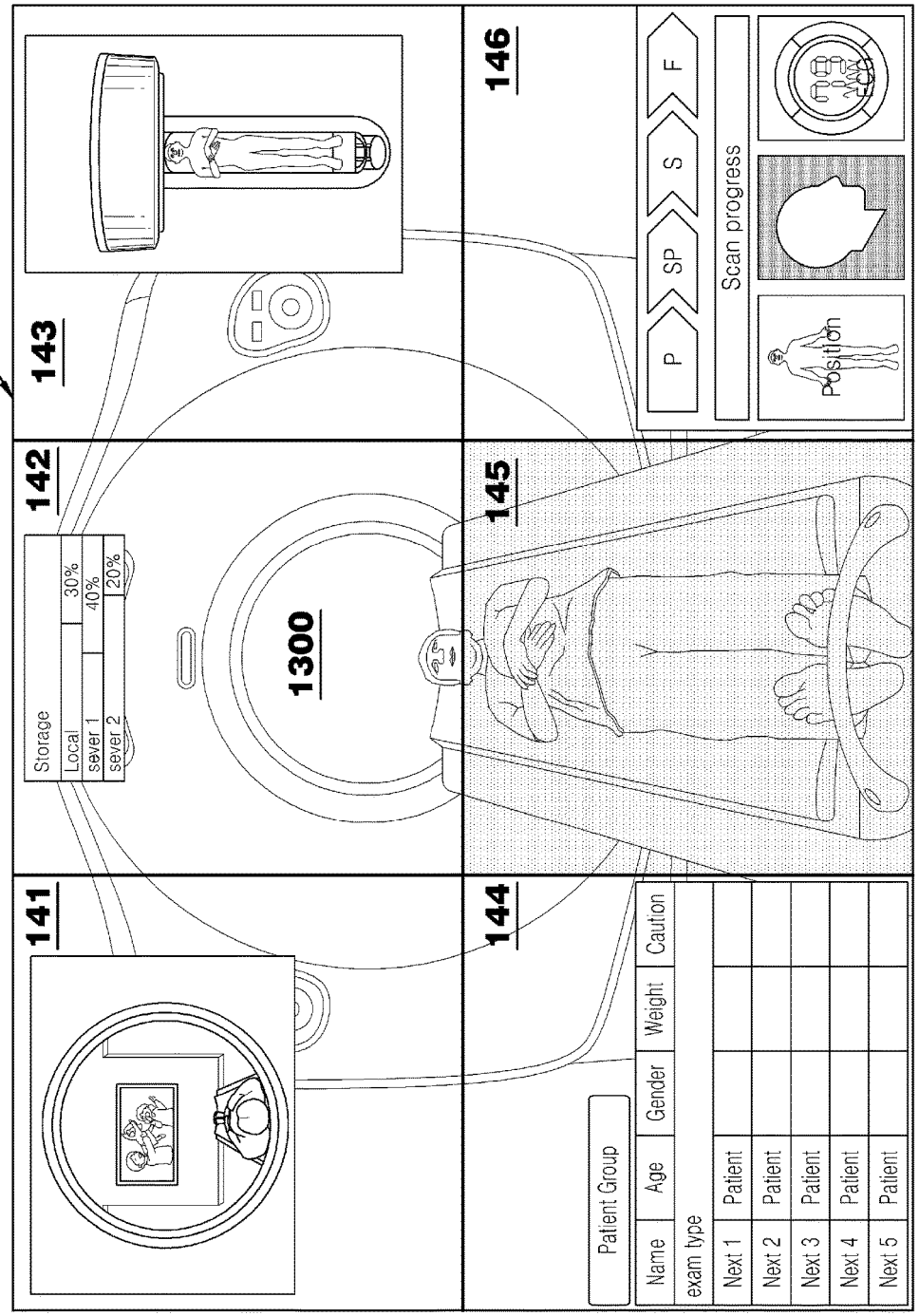
FIG. 13 is a view illustrating a plurality of display units of a console room window, according to an exemplary embodiment.

FIG. 13 is a view illustrating a plurality of display units of the console room window 140, according to an exemplary embodiment.

In FIG. 13, the apparatus 100 includes six display units 141, 142, 143, 144, 145, and 146 constituting the console room window 140. The six display units 141, 142, 143, 144, 145, and 146 may be arranged adjacent to one another, and the apparatus 100 may separately control the six display units 141, 142, 143, 144, 145, and 146.

The apparatus 100 may select an area corresponding to any one of the six display units 141, 142, 143, 144, 145, and 146 of the console room window 140. Next, the apparatus 100 may set the selected area as an information providing area matched to diagnostic information.

For example, the apparatus 100 may obtain diagnostic information about an image obtained by photographing a movement path of the diagnostic table, and may set a right upper area corresponding to the display unit 143 from among all areas of the console room window 140 as an information providing area. Next, the apparatus 100 may output and display the image of the movement path on the display unit 143 on the right upper area of the console room window 140.

Diagnostic information about a list of patients shown on a left lower area of the console room window 140 may need to be displayed on an area larger than a left lower area corresponding to the display unit 144 on the console room window 140. Accordingly, the apparatus 100 may display the diagnostic information about a list of patients by using not only the left lower area corresponding to the display unit 144 but also at least a part of other areas, e.g., a left upper area corresponding to the display unit 141.

The apparatus 100 may set an area corresponding to any one of the six display units 141, 142, 143, 144, 145, and 146 as an observation area. That is, the apparatus 100 may set a lower area 1300 corresponding to the display unit 145 from among all of the areas of the console room window 140 as an observation area. Accordingly, when new diagnostic information is obtained, the apparatus 100 may display the new diagnostic information on an area other than the lower area 1300 that is set as the observation area.

Alternatively, when a user input or new diagnostic information is obtained, the apparatus 100 may use the lower area 1300 as an information providing area. That is, the apparatus 100 may initially set a portion or the whole of the console room window 140 as an information providing area or an observation area, may adjust the initially set information providing area or observation area to a new information providing area, and may use the new information providing area as an area for displaying diagnostic information.

Figure 14:
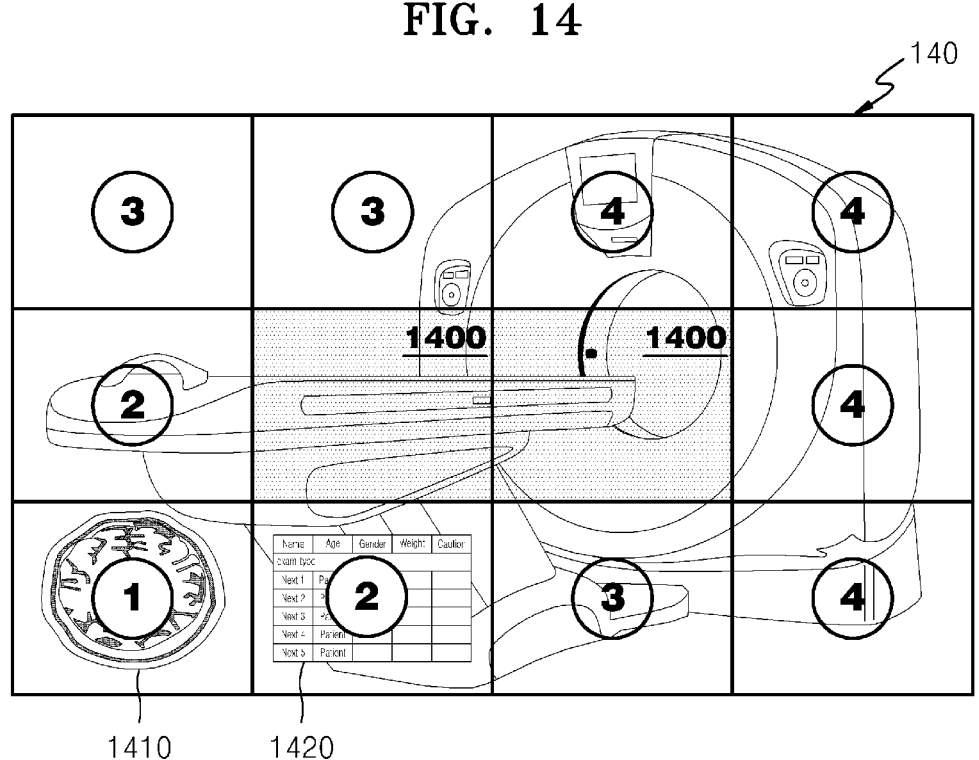
FIG. 14 is a view illustrating a process of providing diagnostic information according to priorities of a plurality of information providing areas, according to an exemplary embodiment.

FIG. 14 is a view illustrating a process of providing diagnostic information according to priorities of a plurality of information providing areas, according to an exemplary embodiment.

The apparatus 100 may set priorities of a plurality of sub-areas on the console room window 140, and may output diagnostic information according to the priorities. In FIG. 14, the apparatus 100 divides the whole of the console room window 140 into 12 sub-areas.

In one embodiment, the apparatus 100 may set two sub-areas 1400 located on a central portion of the console room window 140 from among the 12 sub-areas as an observation area. Next, the apparatus 100 may set priorities of remaining 10 sub-areas excluding the observation area.

The apparatus 100 may set priorities according to a user input, or may determine priorities according to a detected position of the user 5. For example, the apparatus 100 may set a higher priority to a sub-area closer to the detected position of the user 5.

The apparatus 100 may set the same priority to one or more sub-areas. In FIG. 14, the apparatus 100 may set a highest priority "1" to a sub-area 1410 which is a left lower area of the console room window 140 according to the user input or the detected position of the user 5, and may set priorities "2", "3", "4" to the remaining sub-areas of the console room window 140 except for the two sub-areas set as the observation area.

Next, the apparatus 100 obtains diagnostic information about a medial image, and sets the sub-area 1410 to which the highest priority "1" is matched as an information providing area. The apparatus 100 may display the diagnostic information about the medical image on the sub-area 1410 of the console room window 140.

Next, the apparatus 100 may obtain diagnostic information about a list of patients, and may set a sub-area 1420 to which a second-highest priority "2" is matched to an information providing area. Next, the apparatus 100 may display the diagnostic information about the list of patients on the sub-area 1420.

The apparatus 100 may select any one of a plurality of sub-areas having the same priority. In FIG. 14, the apparatus 100 selects a lower sub-area 1420 of the console room window 140 as an information providing area from among two sub-areas to which the same priority "2" is matched.

For example, the apparatus 100 may set a sub-area closer to a position of the user 5 from among sub-areas having the same priority as an information providing area for displaying diagnostic information. Also, the apparatus 100 may set an information providing area for displaying diagnostic information based on a user input that selects a sub-area corresponding to any one of a plurality of sub-areas.

Figure 15:
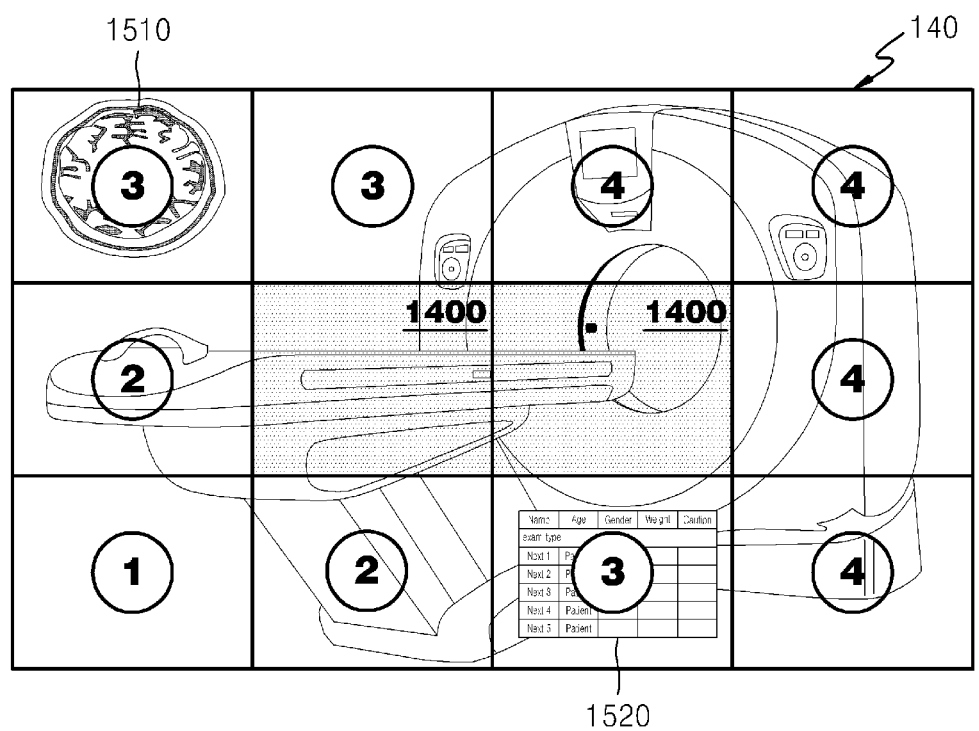
FIG. 15 is a view illustrating a process of providing diagnostic information according to an importance of diagnostic information, according to an exemplary embodiment.

FIG. 15 is a view illustrating a process of providing diagnostic information according to an importance of the diagnostic information, according to an exemplary embodiment.

In FIG. 15, the process of providing diagnostic information according to an importance of the diagnostic information may be performed after the process described with reference to FIG. 14. Alternatively, the process of FIG. 15 may be performed irrespective of the process of FIG. 14. Similar to FIG. 14, the apparatus 100 divides the console room window 140 into 12 sub-areas. The apparatus 100 may set priorities to 10 sub-areas excluding an observation area according to a predetermined standard, e.g., a user input or a detected position of the user 5 as described in FIG. 14.

In FIG. 15, the apparatus 100 may set or change the information providing area based on an importance of diagnostic information. For example, the apparatus 100 may check importances of pieces of diagnostic information displayed on the sub-area 1410 and the sub-area 1420 of the console room window 140. Next, the apparatus 100 may change information providing areas on which the two pieces of diagnostic information are to be displayed to a sub-area 1510 and a sub-area 1520 according to the checked importances.

For example, the apparatus 100 may previously store an importance matched to each type of diagnostic information. The apparatus 100 may obtain diagnostic information, and may determine an importance of the diagnostic information by checking a preset matching relationship. In FIG. 15, the apparatus 100 determines that diagnostic information about a medical image and diagnostic information about a list of patients each have an importance of "3".

The importance of "3" may correspond to a priority of "3" set to a plurality of sub-areas included in the console room window 140. Accordingly, the apparatus 100 may display two pieces of diagnostic information of the importance of "3" on the sub-area 1510 and the sub-area 1520 to which the priority of "3" is set. Alternatively, the apparatus 100 may select two sub-areas 1510, 1520 from among three areas having the priority of "3" according to a user input or by detecting a position of the user 5.

Although not shown in FIG. 15, the apparatus 100 may additionally obtain diagnostic information about patient information having a highest importance of "1". In this case, the apparatus 100 may display the diagnostic information that is newly obtained on a left lower sub-area of the console room window 140 to which a priority of "1" is matched.

Figure 16:
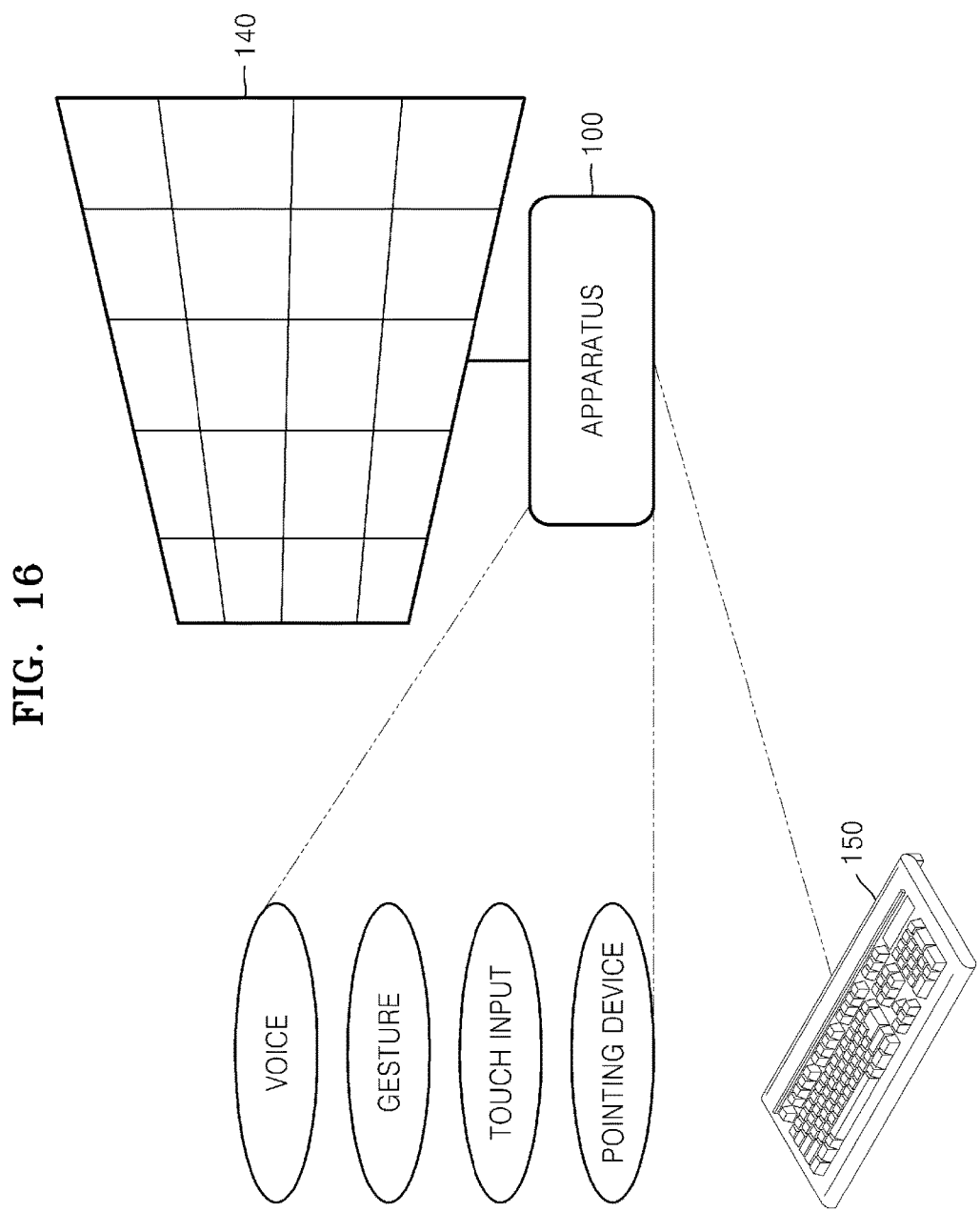
FIG. 16 is a view illustrating a process of setting an information providing area based on a user input, according to an exemplary embodiment.

FIG. 16 is a view illustrating a process of setting an information providing area based on a user input, according to an exemplary embodiment.

The apparatus 100 may detect the user 5, a position of the user 5, a distance between the user 5 and the console room window 140, and a gesture of the user 5 by using various types of sensors included in the sensing unit 160, as described above with reference to FIG. 4. For example, the apparatus 100 may detect the user 5 by using a gesture detection sensor, a distance sensor, a depth sensor, and a position sensor.

Also, the apparatus 100 may receive a user input of the user 5 who is located in the console room. For example, the apparatus 100 may detect a user input by using a voice recognition sensor, a gesture recognition sensor, a touch sensor, or a pointing device recognition sensor.

Alternatively, the apparatus 100 may receive a user input of the user 5 who controls the apparatus 100 by using the user input unit 150 including a keyboard, a keypad, and/or a mouse.

The apparatus 100 may control an information providing area and an observation area of the console room window 140 based on at least one from among the user 5 that is detected and the user input that is received. For example, the apparatus 100 sets the information providing area and the observation area by detecting a position and a distance of the user 5, as described above with reference to FIGS. 3 and 4.

Next, the apparatus 100 may receive a user input such as a voice input, a gesture input, a touch input, or an input using a pointing device which changes the information providing area and the observation area, and may control the information providing area and the observation area based on the user input.

In one embodiment, the apparatus 100 may display diagnostic information on the information providing area determined by detecting the user 5, and may change a position and a size of the diagnostic information according to the user's selection. Accordingly, the apparatus 100 may intuitively provide the diagnostic information to the user 5.

Figure 17:
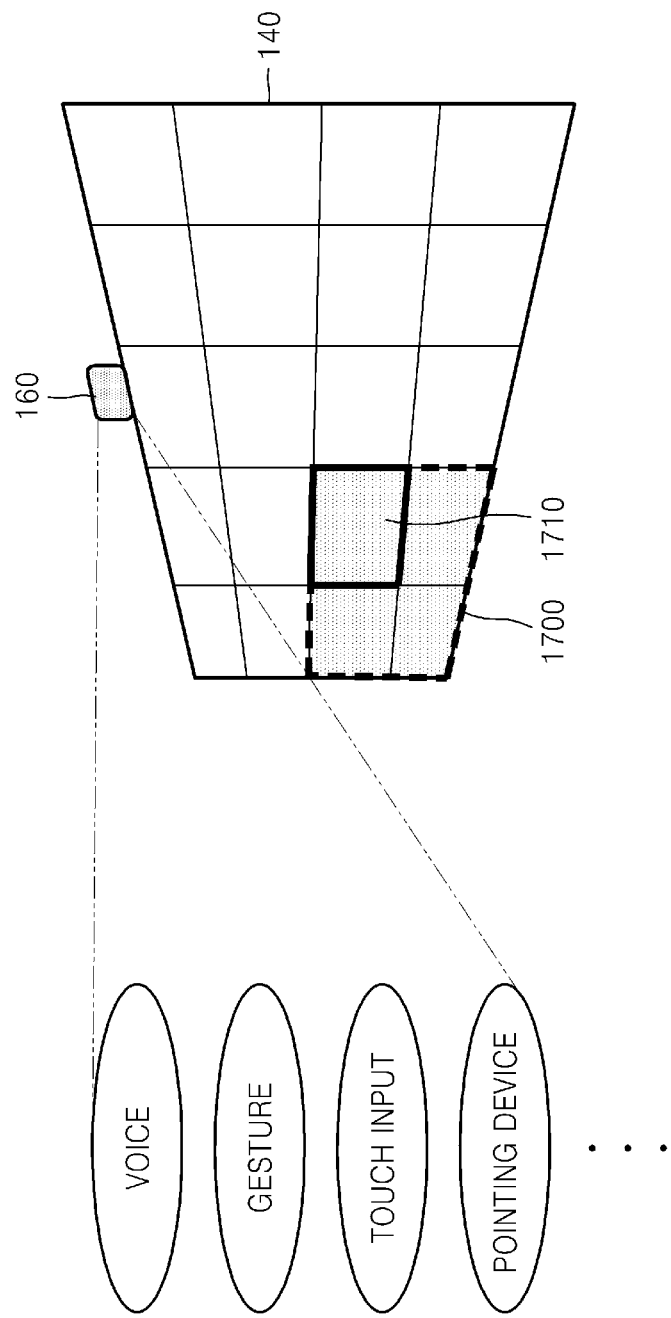
FIG. 17 is a view illustrating a process of setting an information providing area by using a position of a user, according to an exemplary embodiment.

FIG. 17 is a view illustrating a process of setting an information providing area by using a position of the user 5, according to an exemplary embodiment. The details described with reference to FIG. 16 will not be repeated.

The apparatus 100 may detect the user 5 who is located in the console room by using the sensing unit 160. Although it is shown in FIG. 17 that the sensing unit 160 is disposed on the console room window 140 and detects the user 5, the position and the shape of the sensing unit 160 are exemplary and exemplary embodiments are not limited thereto.

The apparatus 100 may extract an area of the user 5 by using a detection algorithm that is previously stored from an image obtained by capturing the inside of the console room. For example, the apparatus 100 may use various types of programs and algorithms such as a color detection algorithm and a pattern detection algorithm.

Alternatively, the apparatus 100 may detect the user 5 by recognizing a gesture of the user 5. That is, when the user 5 makes a gesture matching a gesture that is previously stored, the apparatus 100 may detect a movement of the user, e.g., a hand movement or a body movement of the user 5 and may receive the detected hand movement or body movement as a user input.

In one embodiment, the apparatus 100 may use an identification device or an ID tag to detect the user 5. That is, the apparatus 100 may information about a position and a distance of the user 5 by detecting a pass or an ID card of the user 5.

As shown in FIG. 17, as the position and the distance of the user 5 are detected, the apparatus 100 may reduce an information providing area 1700 to an area 1710. A process of detecting the user 5 and adjusting an information providing area will now be explained in detail with reference to FIG. 18.

Figure 18:
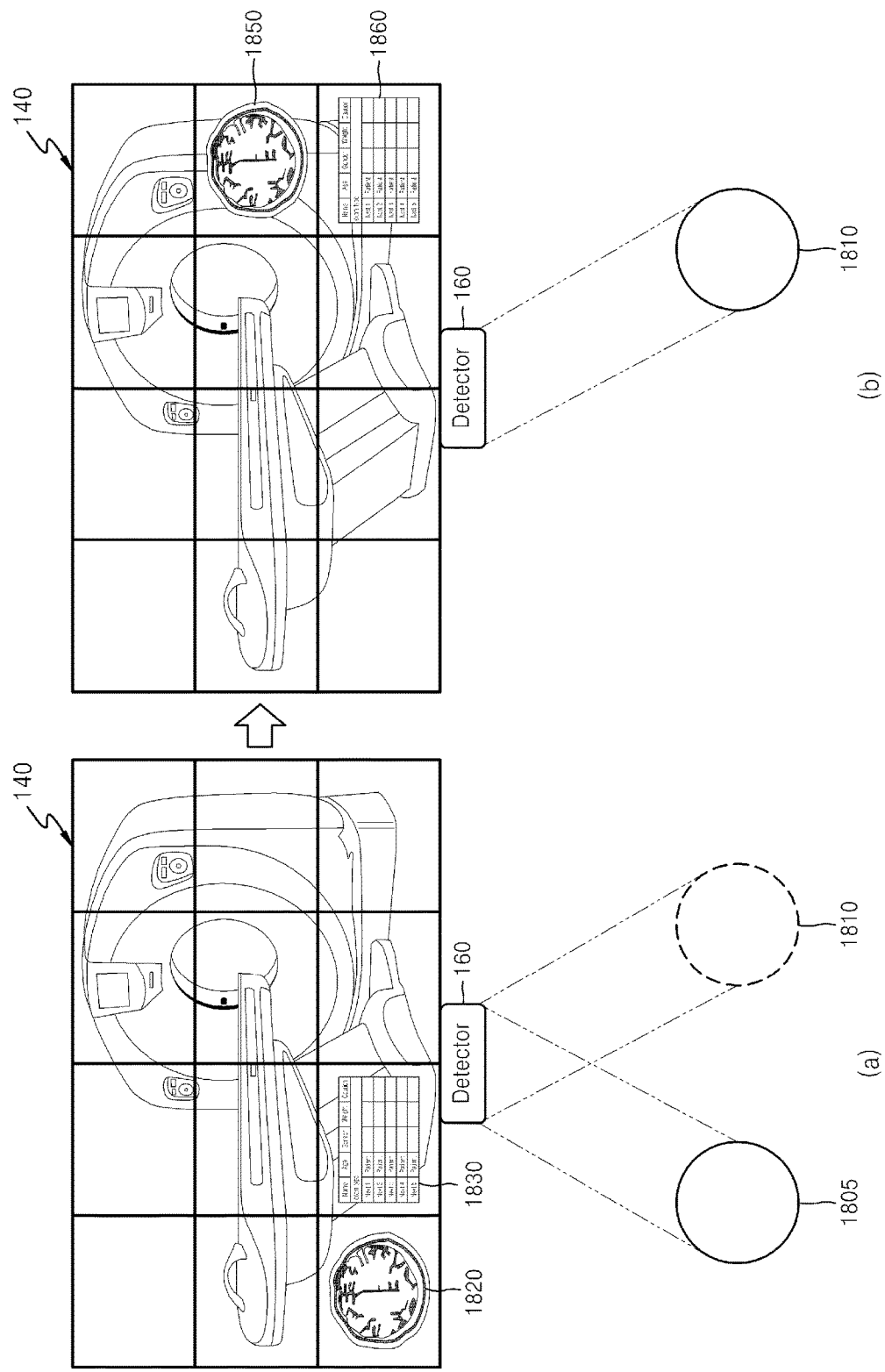
FIG. 18 is a view illustrating a process of setting an information providing area by detecting a position of a user, according to an exemplary embodiment.

FIG. 18 is a view illustrating a process of setting an information providing area by detecting a position of the user 5, according to an exemplary embodiment. A position and a shape of the sensing unit 160 shown in FIG. 18 are exemplary, and exemplary embodiments are not limited thereto.

In FIG. 18(*a*), the apparatus 100 detects the object 10 by using the sensing unit 160. The apparatus 100 may detect the user 5 who is located at a position 1805 that is in a left side from the center of the console room window 140. Accordingly, the apparatus 100 displays two pieces of obtained diagnostic information on a sub-area 1820 and a sub-area 1830 located at a left side of the console room window 140. Next, the user 5 moves from the position 1805 to a position 1810.

In FIG. 18(*b*), the apparatus 100 may detect the user 5 who is located at the position 1810. Accordingly, the apparatus 100 may change positions of the two pieces of diagnostic information displayed on the sub-area 1820 and the sub-area 1830.

That is, the apparatus 100 may set a sub-area 1850 and a sub-area 1860 which are closer to the position 1810 as a new information providing area for displaying diagnostic information, and may display the two pieces of diagnostic information on the sub-area 1850 and the sub-area 1860.

The apparatus 100 may adjust a size of an information providing area according to a position and a distance of the user 5. For example, when the user 5 is located on the position 1805, the apparatus 100 may reduce a size of an information providing area corresponding to the sub-area 1820 and the sub-area 1830 to be less than when the user 5 is located on the position 1810. In other words, the apparatus 100 may adjust an information providing area that is closer to the user 5 to have a smaller size.

On the other hand, when the user 5 is located on the position 1810, the apparatus 100 may set a size of an information providing area corresponding to the sub-area 1850 and the sub-area 1860 to be less than when the user 5 is located on the position 1805. Accordingly, the apparatus 100 may provide diagnostic information having a relative constant size to the user 5 even when a distance of the user 5 from the center of the console room window 140 is changed.

Alternatively, the apparatus 100 may change a priority of the information providing area based on a position of the user 5. That is, when the user 5 is located at the position 1805, the apparatus 100 may set priorities of the sub-area 1820 and the sub-area 1830 to be higher than those of right sub-areas of the console room window 140. Accordingly, the apparatus 100 may display newly obtained diagnostic information on a sub-area closer to the user 5 on the console room window 140.

Next, when the user 5 moves from the position 1805 to the position 1810, the apparatus 100 may adjust priorities of the sub-area 1850 and the sub-area 1860 to be higher than those of the sub-area 1820 and the sub-area 1830. Accordingly, the apparatus 100 may display diagnostic information that is additionally obtained on a right side of the console room window 140 so that the user 5 may conveniently check the additionally obtained diagnostic information.

Figure 19:
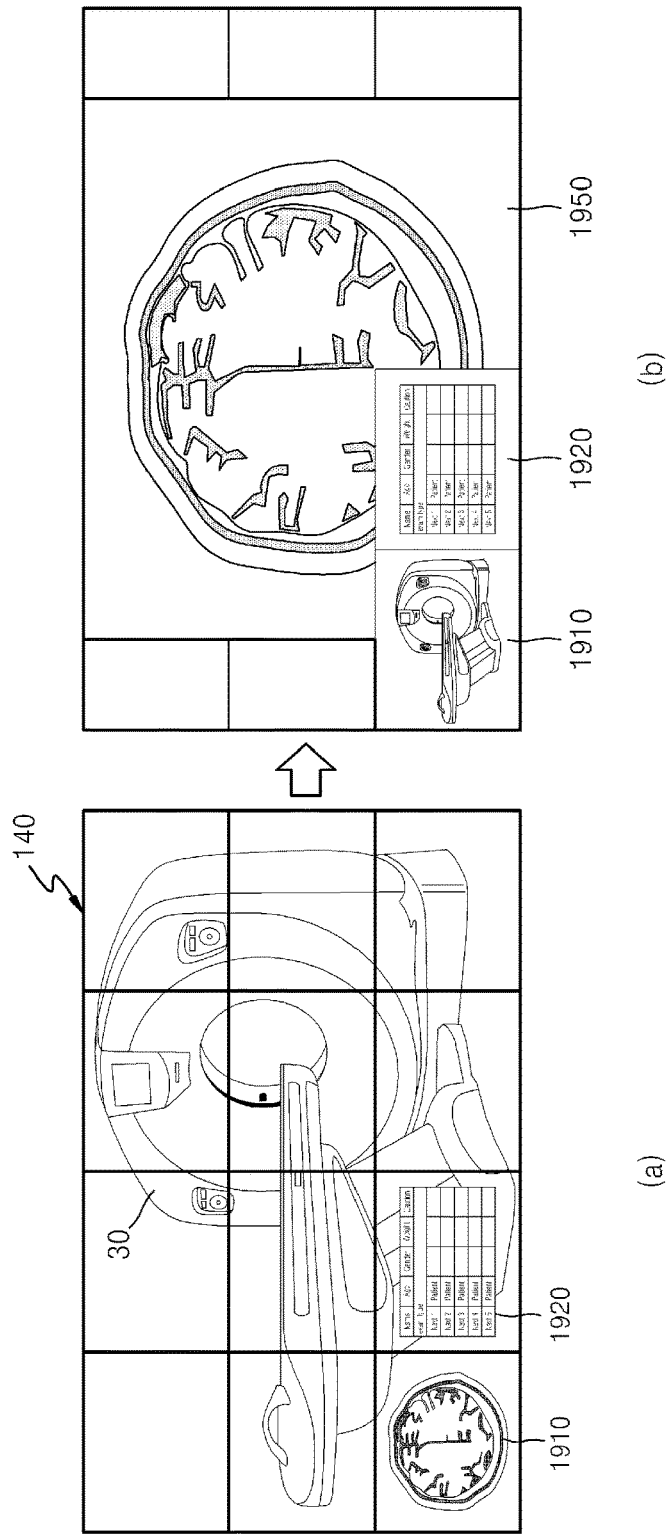
FIG. 19 is a view illustrating a process of displaying diagnostic information on a console room window, according to an exemplary embodiment.

FIG. 19 is a view illustrating a process of displaying diagnostic information on the console room window 140, according to an exemplary embodiment.

In FIG. 19(*a*), the apparatus 100 displays diagnostic information on a sub-area 1910 and a sub-area 1920. The apparatus 100 respectively displays diagnostic information about a medical image on the sub-area 1910 and diagnostic information about a list of patients on the sub-area 1920. The apparatus 100 may set sub-areas excluding the sub-area 1910 and the sub-area 1920 from among all sub-areas of the console room window 140 as an observation area. Accordingly, the user 5 may observe the medical diagnostic system 30 through the observation area on which no diagnostic information is displayed.

In FIG. 19(*b*), the apparatus 100 enlarges and outputs the diagnostic information about the medical image displayed on the sub-area 1910. That is, the apparatus 100 may receive a user input that requests the medical image to be enlarged, and may enlarge and display the diagnostic information about the medical image displayed on the sub-area 1910 on a portion 1950. On the other hand, the apparatus 100 may display the diagnostic information about the medical image on the whole console room window 140.

The apparatus 100 may continuously display the diagnostic information about the list of patients on the sub-area 1920. On the other hand, the apparatus 100 may display an image obtained by photographing the inside of the shield room on the sub-area 1910. That is, the apparatus 100 may output diagnostic information about the inner area of the shield room (i.e., an image obtained by photographing the inside of the shield room) to the sub-area 1910 on which the diagnostic information about the medical image was previously displayed so that the user 5 may continuously observe the inside of the shield room. Accordingly, the user 5 may simultaneously check the diagnostic information and recognize a condition of the inside of the shield room.

The apparatus 100 may display the two pieces of diagnostic information displayed on the sub-area 1910 and the sub-area 1920 such that the two pieces of diagnostic information overlap with the diagnostic information displayed on the portion 1950 in FIG. 19(*b*). Alternatively, the apparatus 100 may adjust and display transparencies of the two pieces of diagnostic information displayed on the sub-area 1910 and the sub-area 1920.

Figure 20:
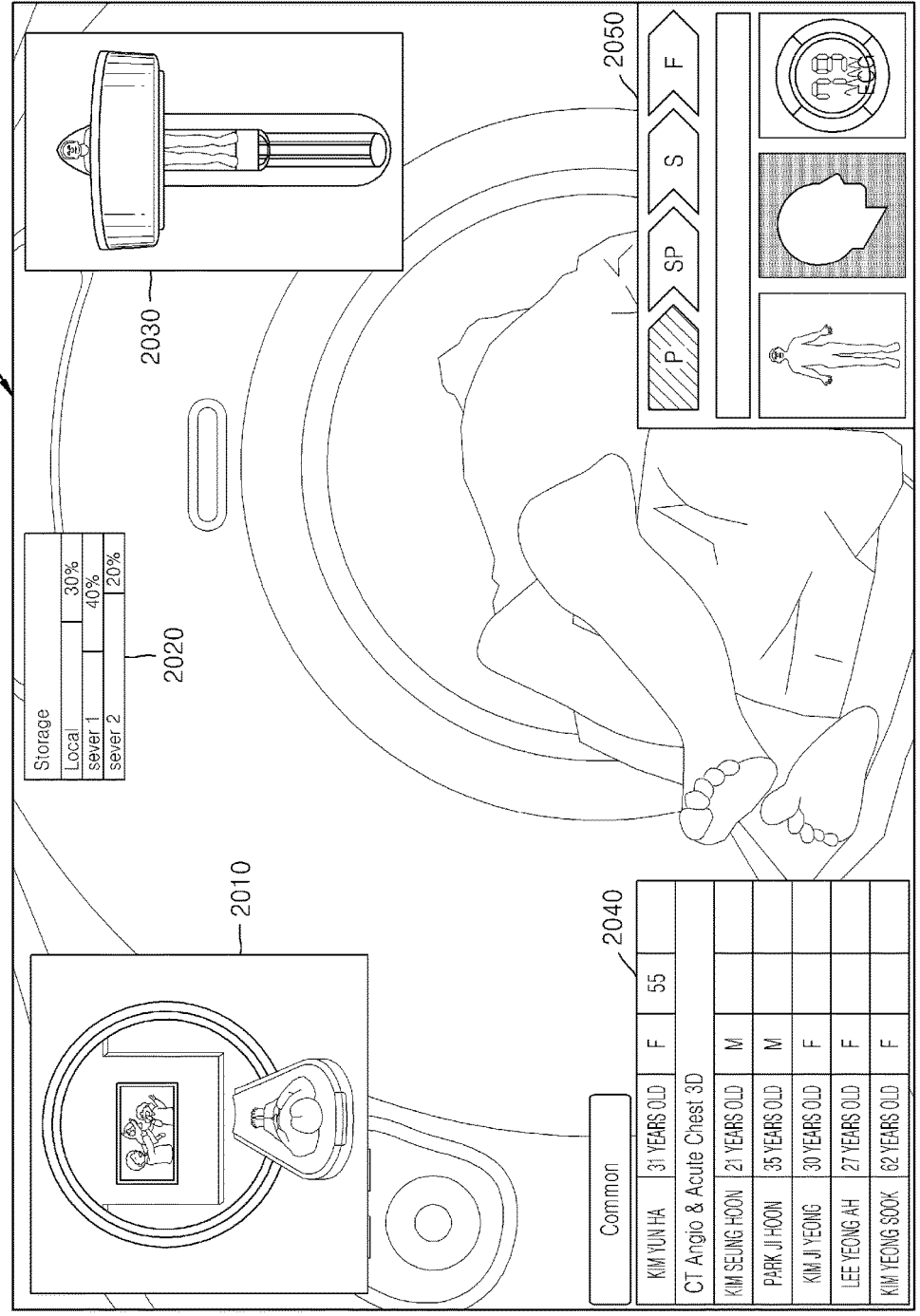
FIG. 20 is a view illustrating various diagnostic information displayed on a console room window, according to an exemplary embodiment.

FIG. 20 is a view illustrating various pieces of diagnostic information displayed on the console room window 140, according to an exemplary embodiment.

In FIG. 20, when the object 10 is placed on the diagnostic table of the medical diagnostic system 30, the diagnostic table is moved into the gantry for medical diagnosis. The user 5 may observe a condition according to which the diagnostic table is moved through the console room window 140.

The apparatus 100 may obtain a plurality of diagnostic information, and may set an information providing area and an observation area on the console room window 140. Next, the apparatus 100 may display the diagnostic information on the information providing area and may provide the diagnostic information to the user 5.

In FIG. 20, the apparatus 100 obtains diagnostic information obtained by photographing the inner area of the gantry, diagnostic information about the local memory of the medical diagnostic system 30, diagnostic information obtained by photographing a movement path of the diagnostic table, diagnostic information about a list of patients, and diagnostic information about a state of progress of a protocol. Next, the apparatus 100 may output the five pieces of diagnostic information to information providing areas 2010, 2020, 2030, 2040, and 2050, respectively.

The user may recognize various pieces of information about the object 10 who is being photographed from the diagnostic information about the list of patients displayed on the information providing area 2040. For example, the user 5 may check a name, an age, a gender, a weight, and other specifics of the object 10 (or patient), and may determine whether the object 10 is the same as the patient currently placed on the diagnostic table. Also, the user 5 may recognize information about the object 10 by using the protocol according to which the object 10 is to be photographed.

Next, the user 5 may check whether a part of the object 10 to be diagnosed reaches an appropriate position inside the gantry by observing a path through which the diagnostic table is moved into the inside of the gantry. When preparation for diagnosing the object 10 ends, the apparatus 100 may display information indicating that the currently set protocol may start to be used on the information providing area 2050.

Figure 21:
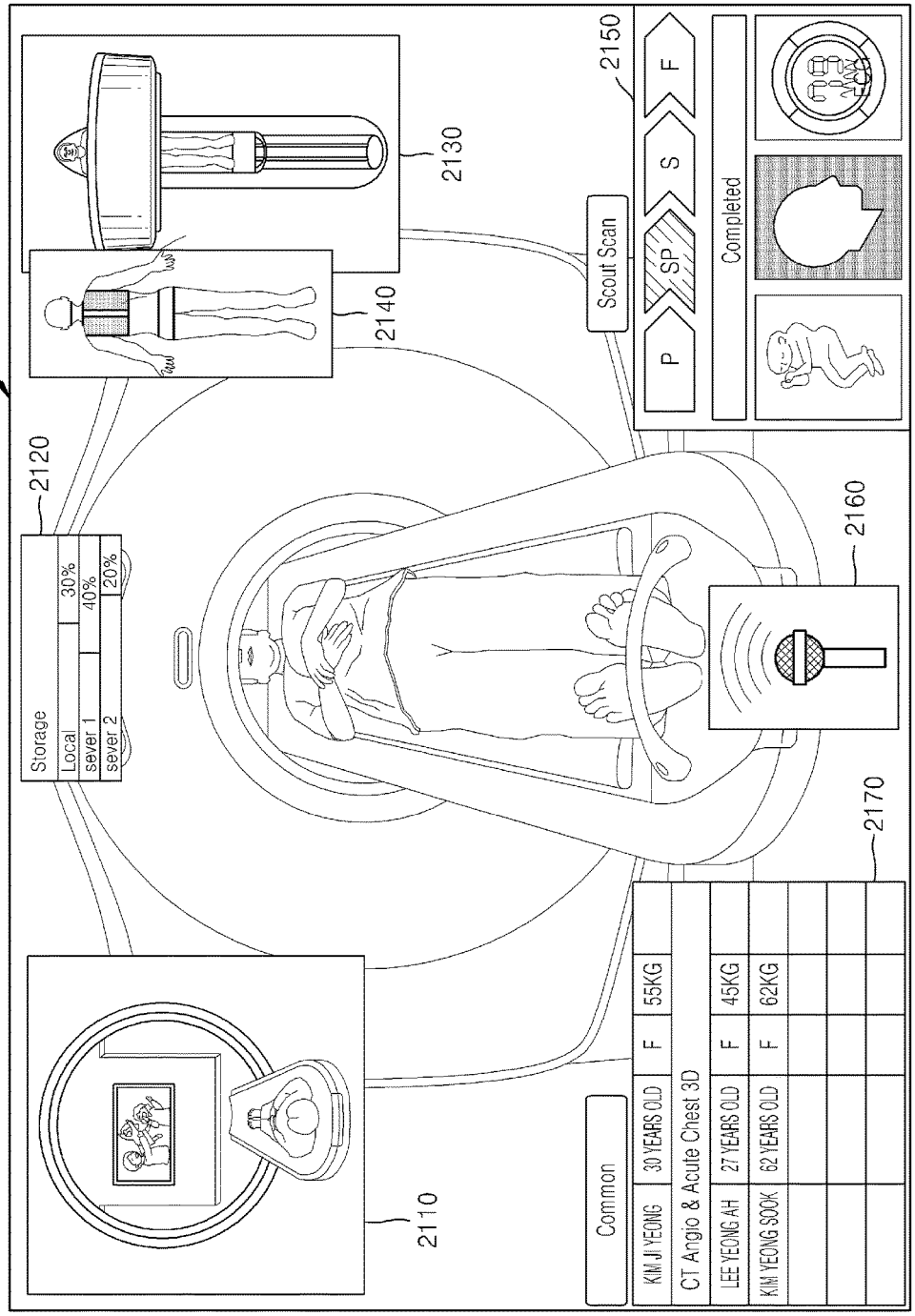
FIG. 21 is a view illustrating various diagnostic information displayed on a console room window, according to another exemplary embodiment.

FIG. 21 is a view illustrating various pieces of diagnostic information displayed on the console room window 140, according to another exemplary embodiment.

In FIG. 21, the apparatus 100 may output the five pieces of diagnostic information described with reference to FIG. 20 to information providing areas 2110, 2120, 2130, 2150, and 2170, respectively. Also, the apparatus 100 may obtain diagnostic information about a radio frequency (RF) coil and diagnostic information about an audio output. The apparatus 100 may display the additionally obtained two pieces of diagnostic information on an information providing area 2140 and an information providing area 2160, respectively.

The apparatus 100 may output, on the information providing area 2140, information about whether an appropriate RF coil is mounted on the part of the object 10 to be diagnosed and information about whether the RF coil is correctly located. Accordingly, the user 5 may check whether to replace the RF coil or adjust a position of the RF coil while observing a condition about the object 10 located in the shield room.

The apparatus 100 may detect whether a microphone located in the console room is activated. Accordingly, the apparatus 100 may display on the information providing area 2160 console room window 140 diagnostic information about an audio output indicating that an audio is output to the object 10 through the microphone (or a speaker) that is located inside of the shield room.

Figure 22:
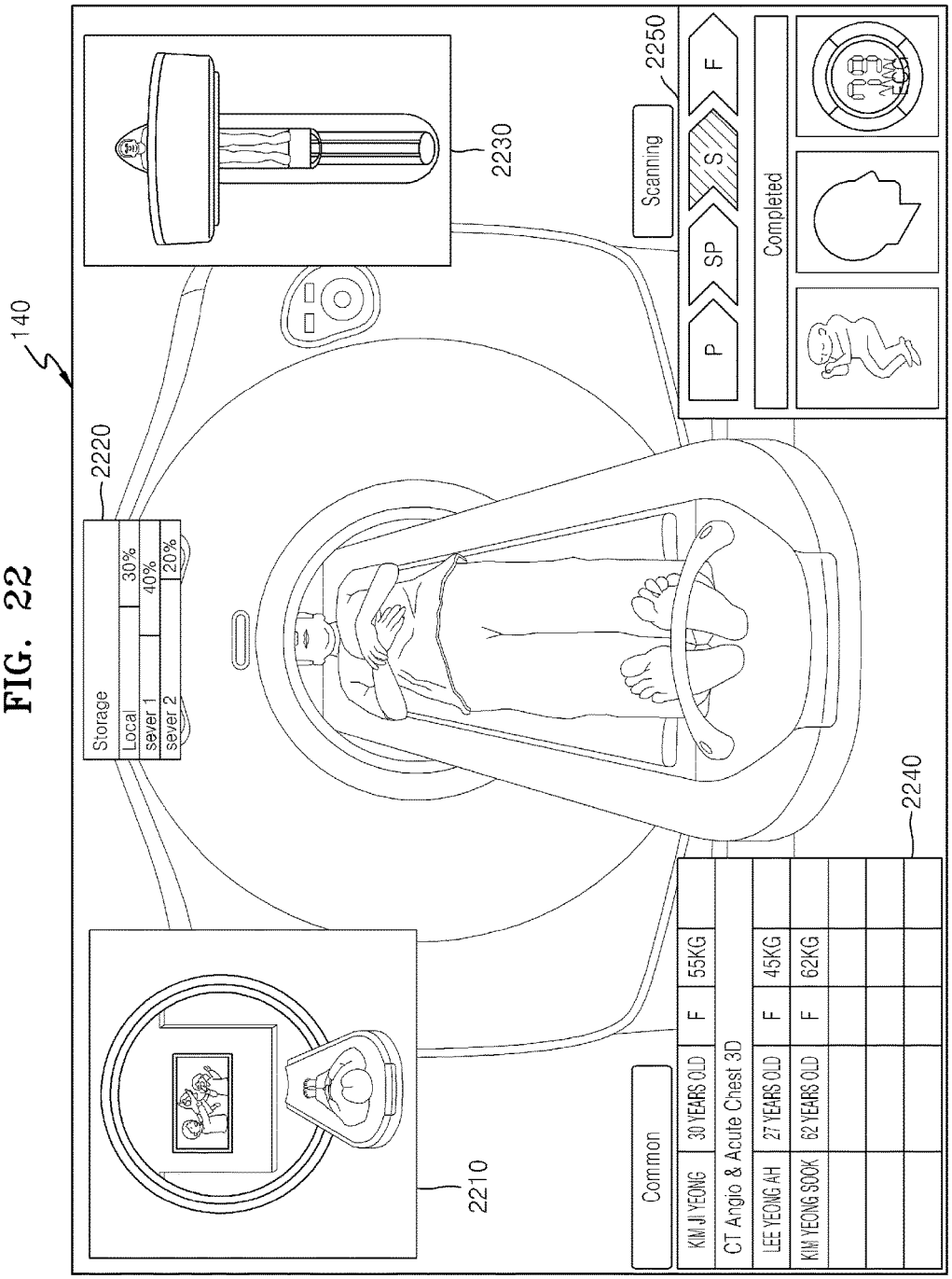
FIG. 22 is a view illustrating various diagnostic information displayed on a console room window, according to still another exemplary embodiment.

FIG. 22 is a view illustrating various pieces of diagnostic information displayed on the console room window 140, according to still another exemplary embodiment.

In FIG. 22, the apparatus 100 may output various pieces of diagnostic information to information providing areas 2210, 2220, 2230, 2240, and 2250, respectively. When a part of the object 10 to be diagnosed is moved to an appropriate position and a diagnostic auxiliary device such as the RF coil is mounted on the part of the object 10, the apparatus 100 may perform a protocol for diagnosing the object 10. Next, the apparatus 100 may receive a signal indicating completion of the protocol from the medical diagnostic system 30, and may update diagnostic information about the protocol displayed on the information providing area 2250.

That is, the apparatus 100 may inform the user 5 that the protocol is completed by outputting a text message "completed" to the information providing area 2250. The apparatus 100 may use various output methods such as a graphic, an audio message, other than the text message.

Figure 23:
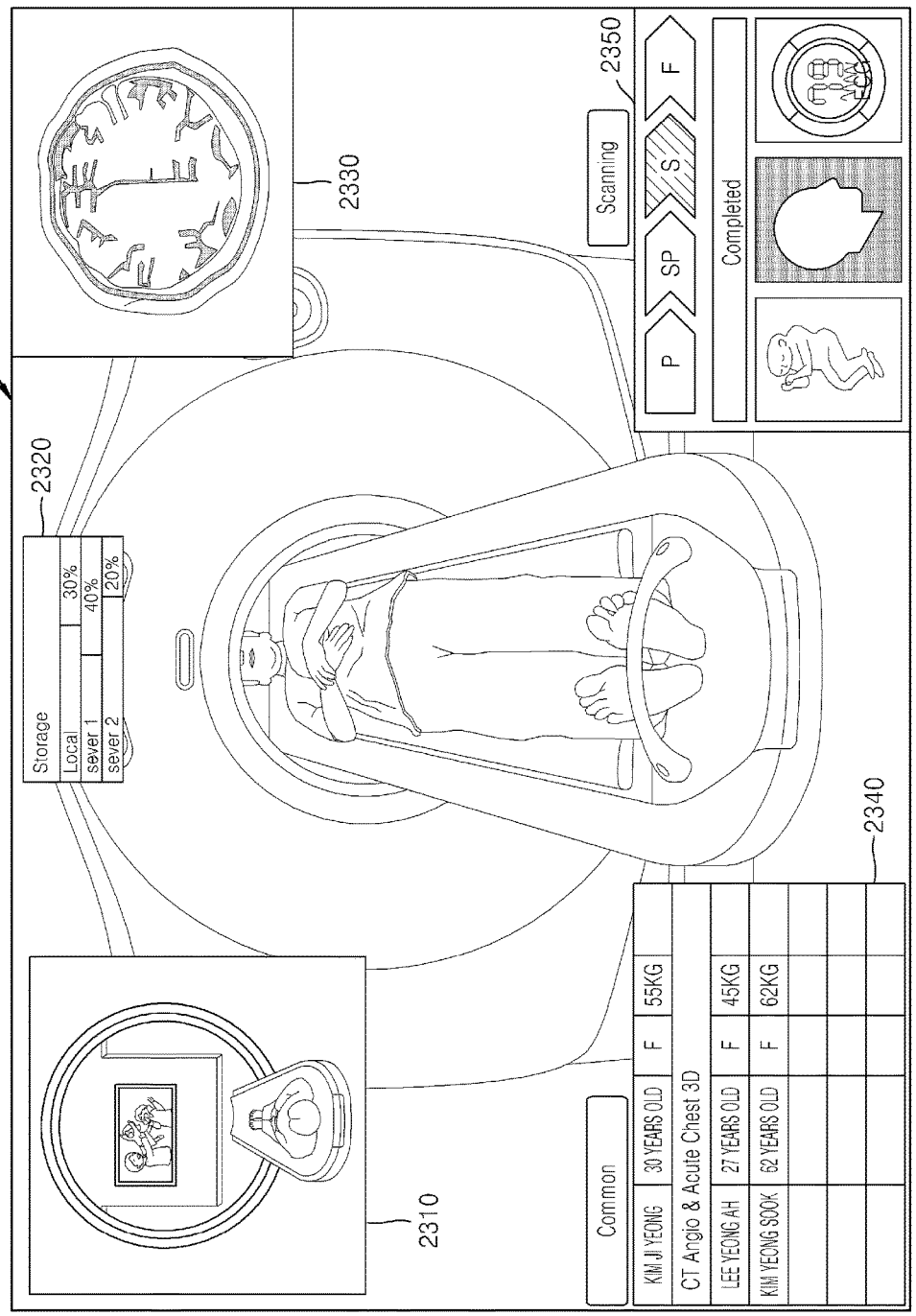
FIG. 23 is a view illustrating various diagnostic information displayed on a console room window, according to still another exemplary embodiment.

FIG. 23 is a view illustrating various pieces of diagnostic information displayed on the console room window 140, according to still another exemplary embodiment.

In FIG. 23, the apparatus 100 obtains diagnostic information about a medical image of the object 10 obtained through a protocol. Next, the apparatus 100 displays the diagnostic information about the medical image on the information providing area 2330. The apparatus 100 may also display other pieces of diagnostic information to information providing areas 2310, 2320, 2340, and 2350, respectively.

In one embodiment, the apparatus 100 may set the information providing area 2330 to overlap with the information providing area 2130 of FIG. 21 (or information providing area 2230 of FIG. 22). The apparatus 100 may set an information providing area matching new diagnostic information in consideration of a size of an observation area that is an empty space of the console room window 140 on which diagnostic information is not displayed. Alternatively, when an importance of the diagnostic information about the medical image is higher than an importance of diagnostic information about a movement path of the diagnostic table, the apparatus 100 may overlap the information providing area 2330 with the information providing area 2130 (or information providing area 2230).

In addition, the apparatus 100 may receive a drag input that selects and drags the information providing area 2330 from the user 5, and move the information providing area 2330 to a position according to the drag input. Alternatively, the apparatus 100 may adjust a position and a size of the information providing area 2330 according to a position of the user 5 and a distance between the user 5 and the console room window 140.

Alternatively, the apparatus 100 may receive a pinch and/or unpinch input that pinches and/or unpinches two positions on the information providing area 2330, and may adjust a size of the information providing area 2330 according to the pinch and/or unpinch input. Also, the apparatus 100 may adjust a transparency of the information providing area 2330.

Figure 24:
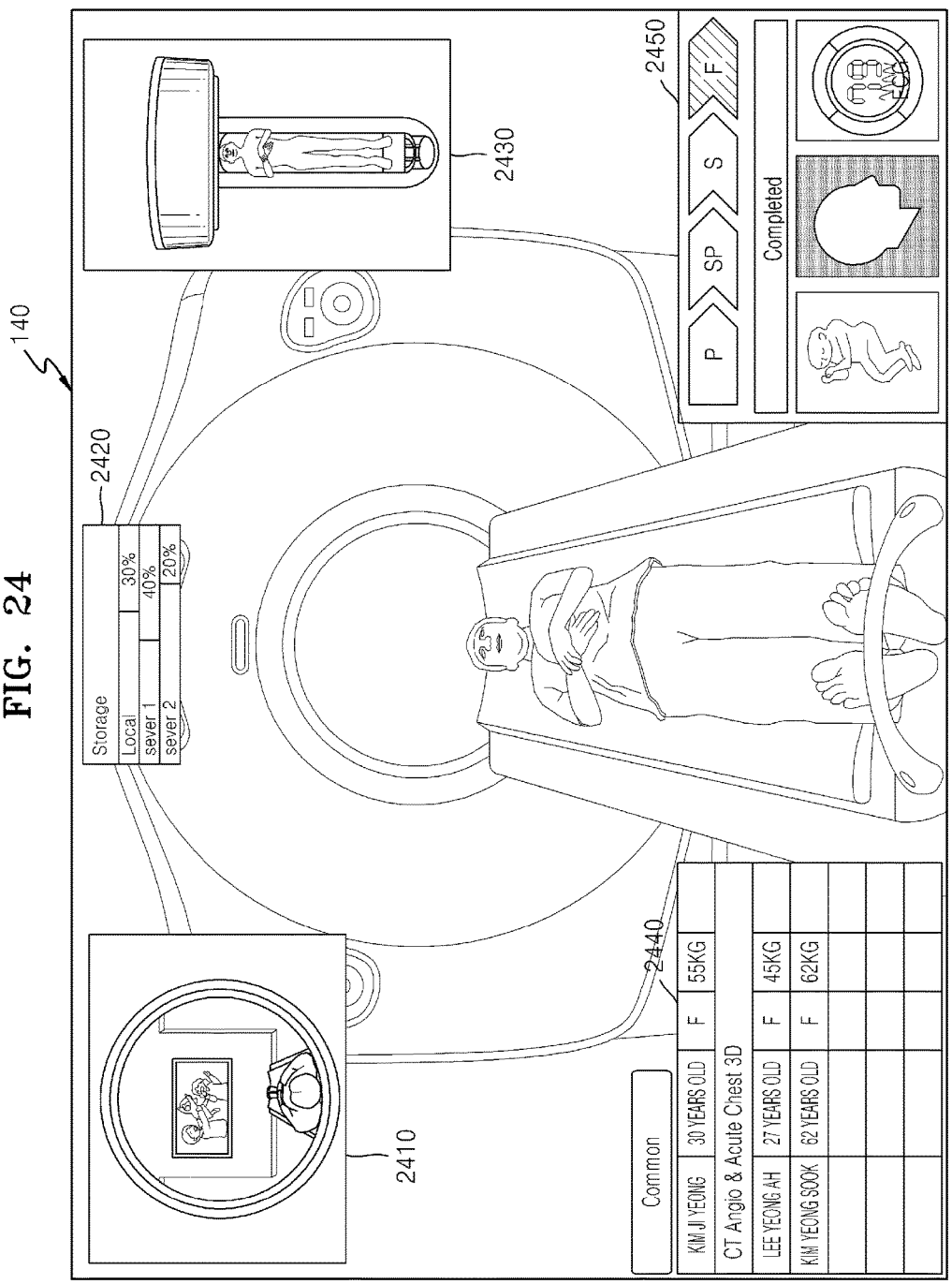
FIG. 24 is a view illustrating various diagnostic information displayed on a console room window, according to still another exemplary embodiment.

FIG. 24 is a view illustrating various pieces of diagnostic information displayed on the console room window 140, according to still another exemplary embodiment.

In FIG. 24, the apparatus 100 may output various pieces of diagnostic information to information providing areas 2410, 2420, 2430, 2440, and 2450, respectively. The apparatus 100 may detect whether diagnosis performed on the object 10 has been completed, and may check information of a next object. Next, the apparatus 100 may output patient information of the next object to a new information providing area (not shown). As shown in FIG. 24, the apparatus 100 may provide patient information such as a name, an age, and a gender of the next object to the user 5. The apparatus 100 may update diagnostic information about a list of patients displayed on the information providing area 2440.

In addition, when there are details of the object 10 which the user 5 needs to recognize to diagnose the object 10, the apparatus 100 may set a portion of an observation area as an information providing area, and may output new diagnostic information. For example, when a contrast agent is used to diagnose the object 10 or when the object 10 needs to undergo an electrocardiogram test, the apparatus 100 may additionally obtain diagnostic information and display the obtained diagnostic information on the portion of the observation area set as the information providing area.

Figure 25:
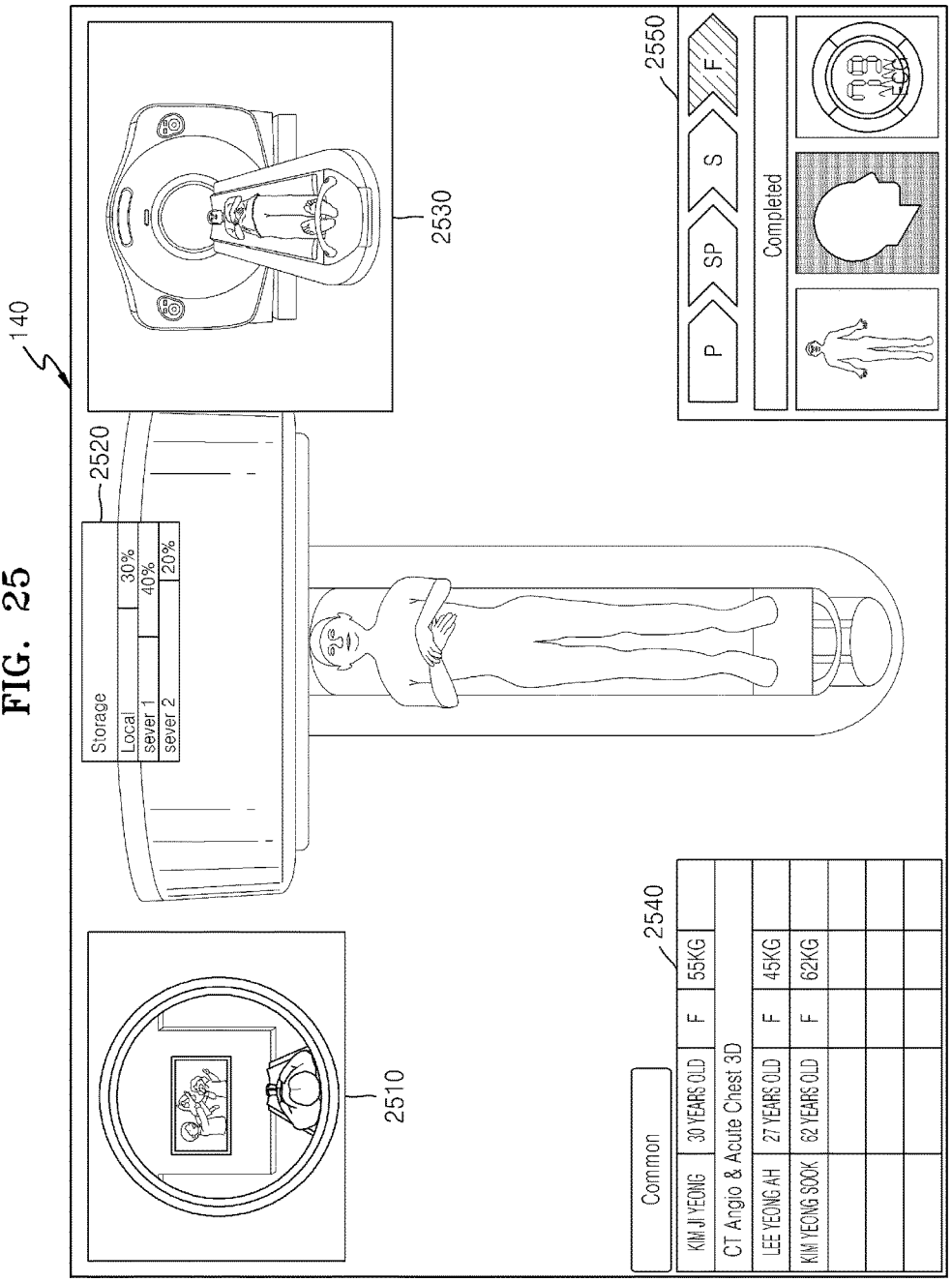
FIG. 25 is a view illustrating various diagnostic information displayed on a console room window, according to still another exemplary embodiment.

FIG. 25 is a view illustrating various pieces of diagnostic information displayed on the console room window 140, according to still another exemplary embodiment.

In FIG. 25, the apparatus 100 may output various pieces of diagnostic information to information providing areas 2510, 2520, 2530, 2540, and 2550, respectively. When diagnosis performed on the object 10 ends, the apparatus 100 may provide diagnostic information about a movement path of the diagnostic table to an observation area of the console room window 140. That is, the apparatus 100 may receive a user input that changes a position of the diagnostic information about the movement path to the observation area, which may be the central portion of the console room window 140 as shown in FIG. 25, and may display the diagnostic information about the movement path on the observation area.

The apparatus 100 may output an image captured by photographing the inside of the shield room so that the user 5 may continuously observe a condition in the inside of the shield room. That is, the apparatus 100 may photograph the inner area of the shield room by using at least one camera, and may display a photographed image on the information providing area 2530. The apparatus 100 may display diagnostic information about the image obtained by photographing the inner area of the shield room on an area on which the diagnostic information about the movement path was previously displayed. Thus, the apparatus 100 may operate such that positions of areas on which two pieces of diagnostic information are displayed are exchanged.

Figure 26:
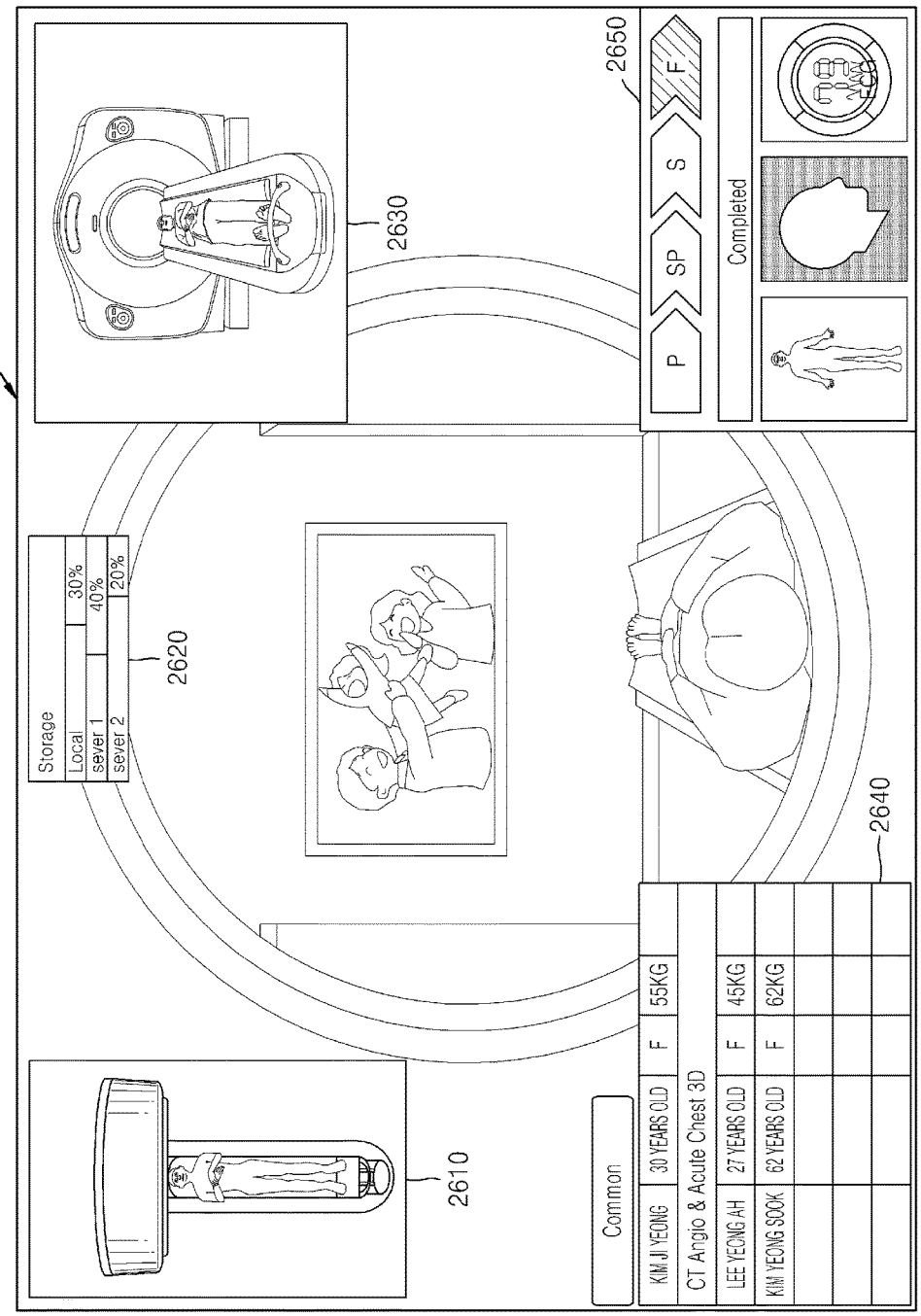
FIG. 26 is a view illustrating various diagnostic information displayed on a console room window, according to still another exemplary embodiment.

FIG. 26 is a view illustrating various pieces of diagnostic information displayed on the console room window 140, according to still another exemplary embodiment.

In FIG. 26, the apparatus 100 may output various pieces of diagnostic information to information providing areas 2610, 2620, 2630, 2640, and 2650, respectively. When the diagnosis ends, the diagnostic table on which the object 10 is placed is moved out of the gantry. Next, the apparatus 100 may display diagnostic information about an image obtained by photographing the inside of the gantry on an observation area of the console room window 140. That is, the apparatus 100 may display the diagnostic information about the movement path of the diagnostic table that was previously displayed on the observation area as shown in FIG. 25 on the information providing area 2610, and the diagnostic information about the inner area of the gantry that was previously displayed on the information providing area 2610 on the observation area.

That is, when the diagnostic table is detected to be moved out of the gantry or a user input is received, the apparatus 100 may change an area on which diagnostic information is displayed. Thus, the diagnostic information about the movement pat of the diagnostic table may be continuously displayed. Accordingly, the user 5 may check, for example, whether the diagnostic table is safely moved from the medical diagnostic system 30 and whether the object 10 stands up from the diagnostic table and walks out of the shield room.

Figure 27:
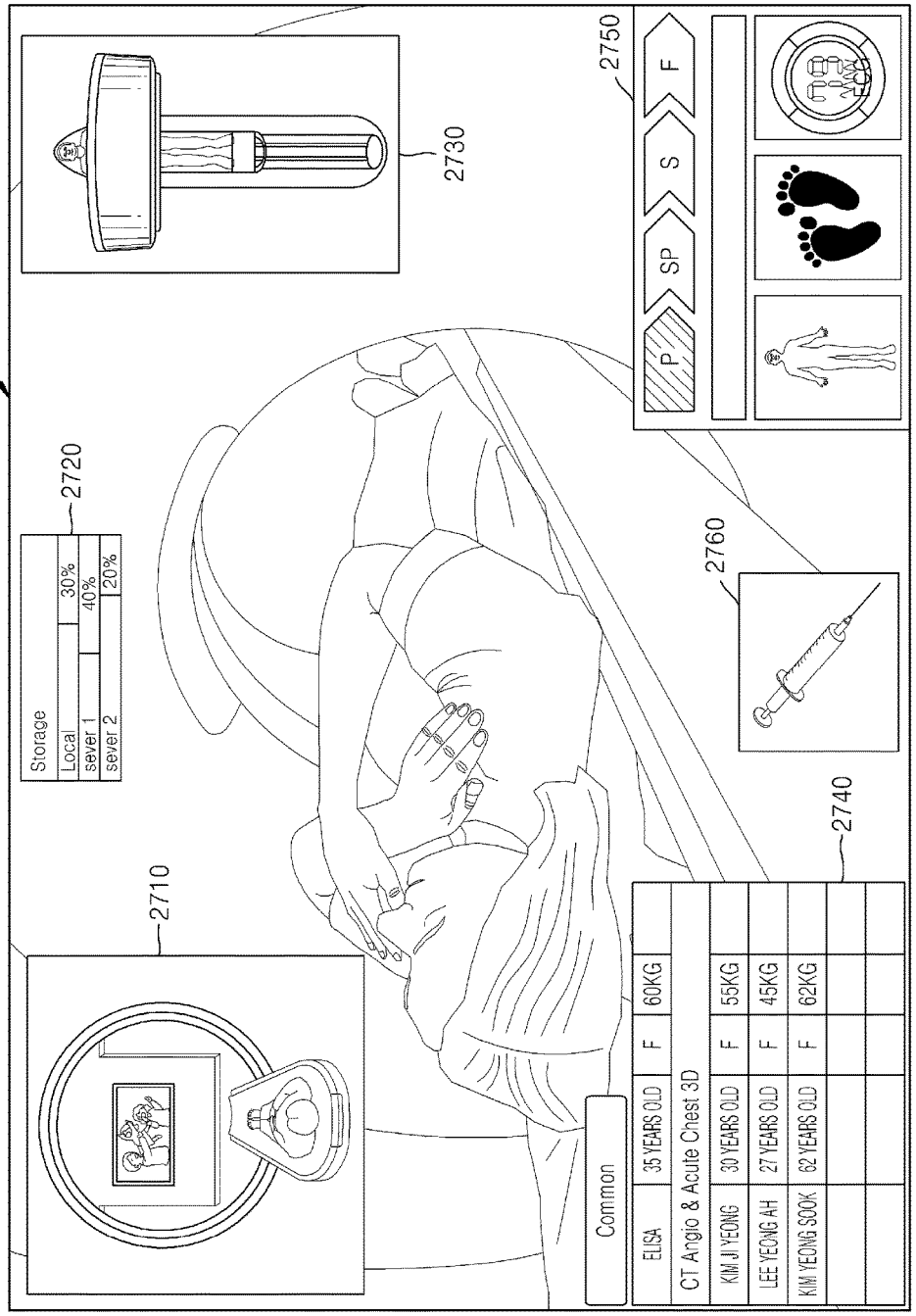
FIG. 27 is a view illustrating various diagnostic information displayed on a console room window, according to still another exemplary embodiment.

FIG. 27 is a view illustrating various pieces of diagnostic information displayed on the console room window 140, according to still another exemplary embodiment.

In FIG. 27, the apparatus 100 may output various pieces of diagnostic information to information providing areas 2710, 2720, 2730, 2740, 2750, and 2760, respectively. The apparatus 100 outputs diagnostic information about a list of patients to the information providing area 2740. When the object 10 needs to be diagnosed by injecting a contrast agent, the apparatus 100 may display diagnostic information indicating that the contrast agent needs to be injected into the object 10 on the information providing area 2760. Also, the apparatus 100 may turn on/off the diagnostic information displayed on the information providing area 2760.

Accordingly, the user 5 may easily recognize important diagnostic information. The apparatus 100 may output a graphic message about the contrast agent to the information providing area 2760. Also, the apparatus 100 output a voice message that is previously stored to inform that the contrast agent is to be injected.

Figure 28:
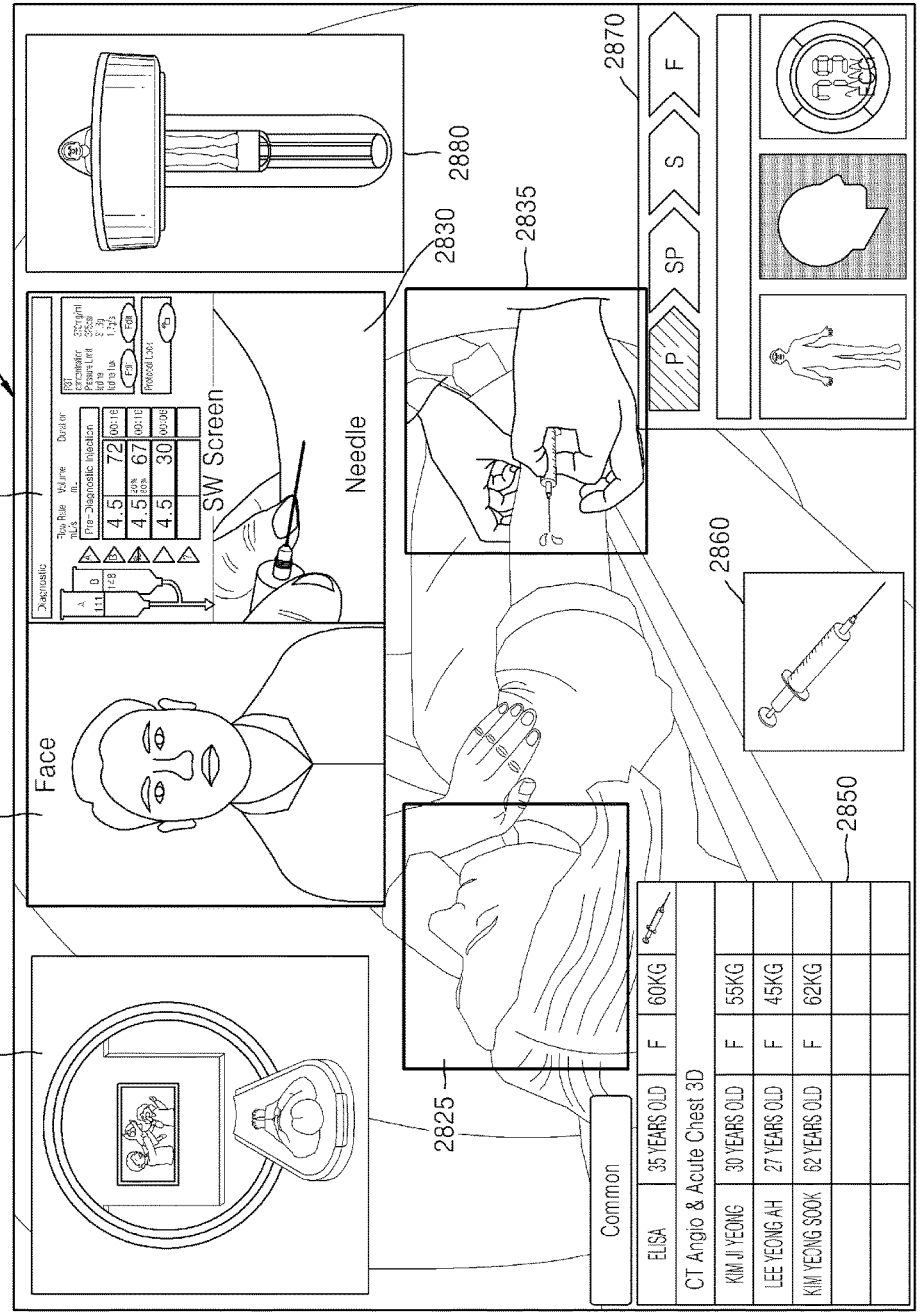
FIG. 28 is a view illustrating various diagnostic information displayed on a console room window, according to still another exemplary embodiment.

FIG. 28 is a view illustrating various pieces of diagnostic information displayed on the console room window 140, according to still another embodiment. In FIG. 28, operations after the exemplary embodiment of FIG. 27 is performed will be explained.

In FIG. 28, the apparatus 100 may output various pieces of diagnostic information to information providing areas 2810, 2820, 2830, 2840, 2850, 2860, 2870, 2880, 2825, and 2835, respectively. The apparatus 100 may obtain an image obtained by photographing a part of the object 10 as diagnostic information, and may provide the diagnostic information to the console room window 140. For example, the apparatus 100 may provide an image obtained by photographing a face of the object 10 or a body part of the object 10 to be diagnosed as diagnostic information.

In FIG. 28, the apparatus 100 photographs the face of the object 10 by using a camera provided in the shield room. Next, the apparatus 100 may output an image obtained by photographing the face of the object 10 as diagnostic information to the information providing area 2820.

Also, the apparatus 100 may photograph an arm of the object 10 to obtain an image of the arm, and may display the image of the arm on the information providing area 2830 of the console room window 140. Furthermore, the apparatus 100 may measure an injection amount and a remaining amount of a contrast agent and bio-monitoring information of the object 10 that varies according to the contrast agent. Next, the apparatus 100 may display diagnosis information about the bio-monitoring information on the information providing area 2840.

In FIG. 28, the user 5 may instantly observe the contrast agent injected into the object 10 through the information providing area 2830 and the information providing area 2840, and may observe a change in the facial expression of the object 10 and a biometric change according to the injection of the contrast agent through the information providing area 2820 and the information providing area 2840.

The apparatus 100 may display the bio-monitoring information to overlap with a part of the object 10 to be diagnosed. That is, the apparatus 100 may display an image obtained by photographing the face of the object 10 on the information providing area 2825 corresponding to the face of the object 10, and may display an image obtained by photographing the arm of the object 10 on the information providing area 2835 corresponding to the arm of the object 10. Accordingly, the user 5 may intuitively recognize the bio-monitoring information. Although not shown in FIG. 28, the apparatus 100 may display diagnostic information about a result obtained after performing, for example, an electrocardiogram test on the object 10 on an information providing area corresponding to the heart of the object 10.

The apparatus 100 may enable the user 5 to simultaneously observe the inner area of the shield room and the bio-monitoring information of the user 5 by adjusting a transparency of diagnostic information that is displayed to overlap with a part of the object 10 to be diagnosed. That is, the apparatus 100 may increase a transparency of diagnostic information that is displayed to overlap with an information providing area corresponding to a body part of the object 10.

Figure 29:
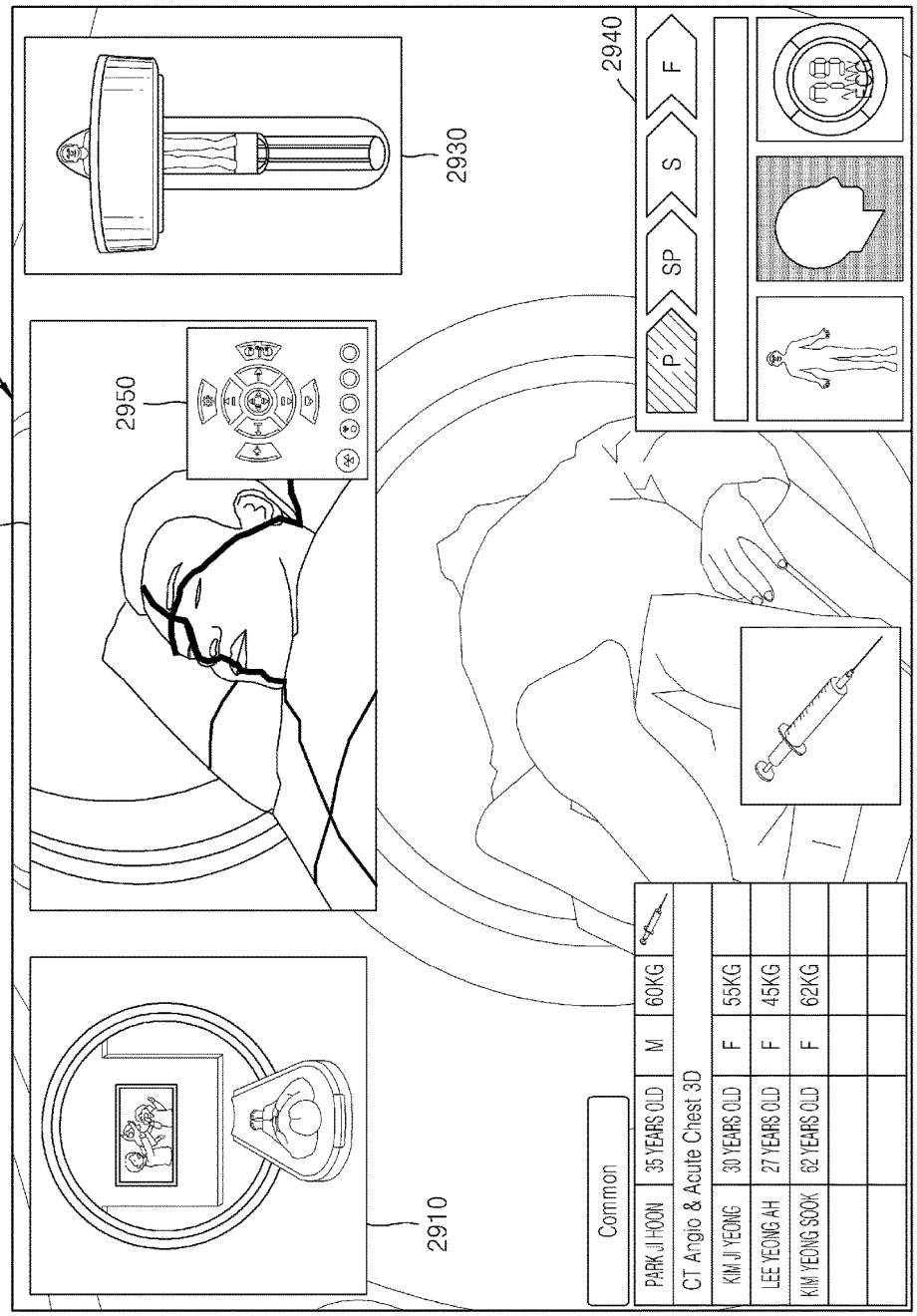
FIG. 29 is a view illustrating various diagnostic information displayed on a console room window, according to still another exemplary embodiment.

FIG. 29 is a view illustrating various pieces of diagnostic information displayed on the console room window 140, according to still another exemplary embodiment.

In FIG. 29, the apparatus 100 may output various pieces of diagnostic information to information providing areas 2910, 2920, 2930, 2940, and 2950, respectively. The medical diagnostic system 30 may perform a zeroing process to diagnose the object 10. The apparatus 100 may output an image obtained by photographing the face of the object 10 to the console room window 140 so that the user 5 may monitor the zeroing process. As shown in FIG. 29, the apparatus 100 may display the image obtained by photographing the face of the object 10 on the information providing area 2920.

The apparatus 100 may display diagnostic information about a control menu on an information providing area 2950. That is, the apparatus 100 may detect a user input that manipulates the control menu displayed on the information providing area 2950, and may transmit a signal for controlling the medical diagnostic system 30 to the medical diagnostic system 30. Accordingly, the user 5 may conveniently perform the zeroing process in the console room without having to enter the shield room to directly manipulate the medical diagnostic system 30.

The apparatus 100 may provide a control menu about an overall function and structure of the medical diagnostic system 30 as well as the control menu about the zeroing process.

Figure 30:
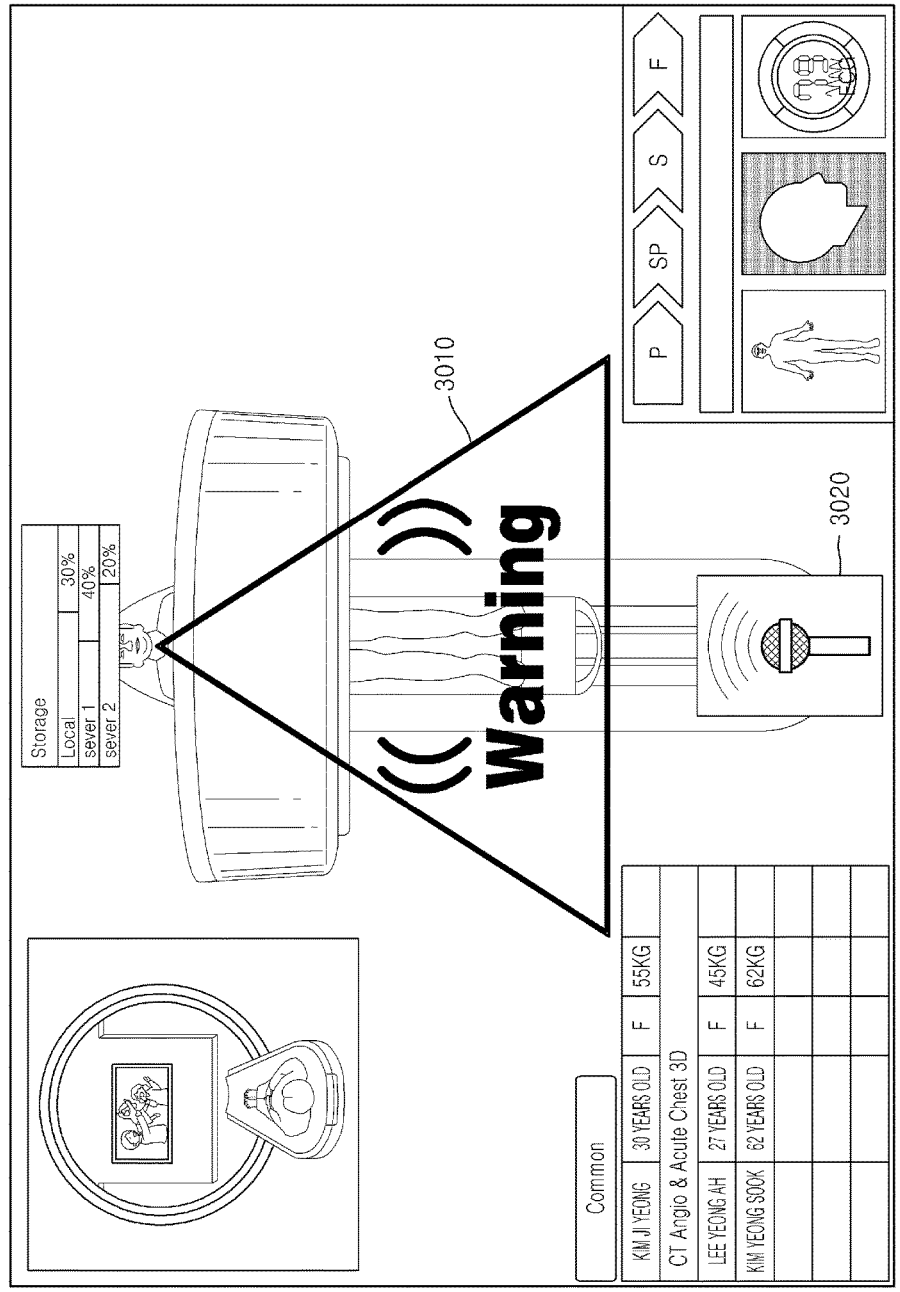
FIG. 30 is a view illustrating various diagnostic information displayed on a console room window, according to still another exemplary embodiment.

FIG. 30 is a view illustrating various pieces of diagnostic information displayed on the console room window 140, according to still another exemplary embodiment.

The apparatus 100 may output a warning message according to an amount of a movement of the object 10 when the object 10 moves during diagnosis. That is, the medical diagnostic system 30 may detect the movement of the object 10 during diagnosis by using various types of sensors. For example, the medical diagnostic system 30 may detect the movement of the object 10 by using a light sensor, a pressure sensor, a magnetic field sensor, a tilt sensor, a frequency sensor, and/or an image sensor.

Furthermore, the medical diagnostic system 30 may check whether an amount of the detected movement is equal to or greater than a critical value that is pre-determined. Next, when the amount of the movement of the object 10 is equal to or greater than the critical value, the medical diagnostic system 30 may transmit a signal indicating that the movement of the object 10 has been detected to the apparatus 100.

The apparatus 100 may receive the signal indicating that the movement of the object 10 has been detected from the medical diagnostic system 30 as diagnostic information, and may output a message indicating that the movement of the object 10 has been detected to the console room window 140.

For example, the apparatus 100 may visually output a message indicating that the movement of the object 10 has been detected on an information providing area 3010 as shown in FIG. 30. Alternatively, the apparatus 100 may notify the user 5 that the movement of the object 10 has been detected by outputting an audio message into the inside of the console room. Furthermore, the apparatus 100 may transmit, for example, an audio message indicating that the object 10 must not move through a speaker located in the inside of the shield room. The apparatus 100 may display diagnostic information indicating that the audio message has been transmitted to the object on an information providing area 3020 of the console room window 140.

The user 5 may receive the diagnostic information from the apparatus 100, and perform an action to control the object 10 not to move during diagnosis. For example, the user 5 may enter the inside of the shield room and may request the object 10 not to move, or may transmit a voice message requesting the same through a microphone into the console room.

Figure 31:
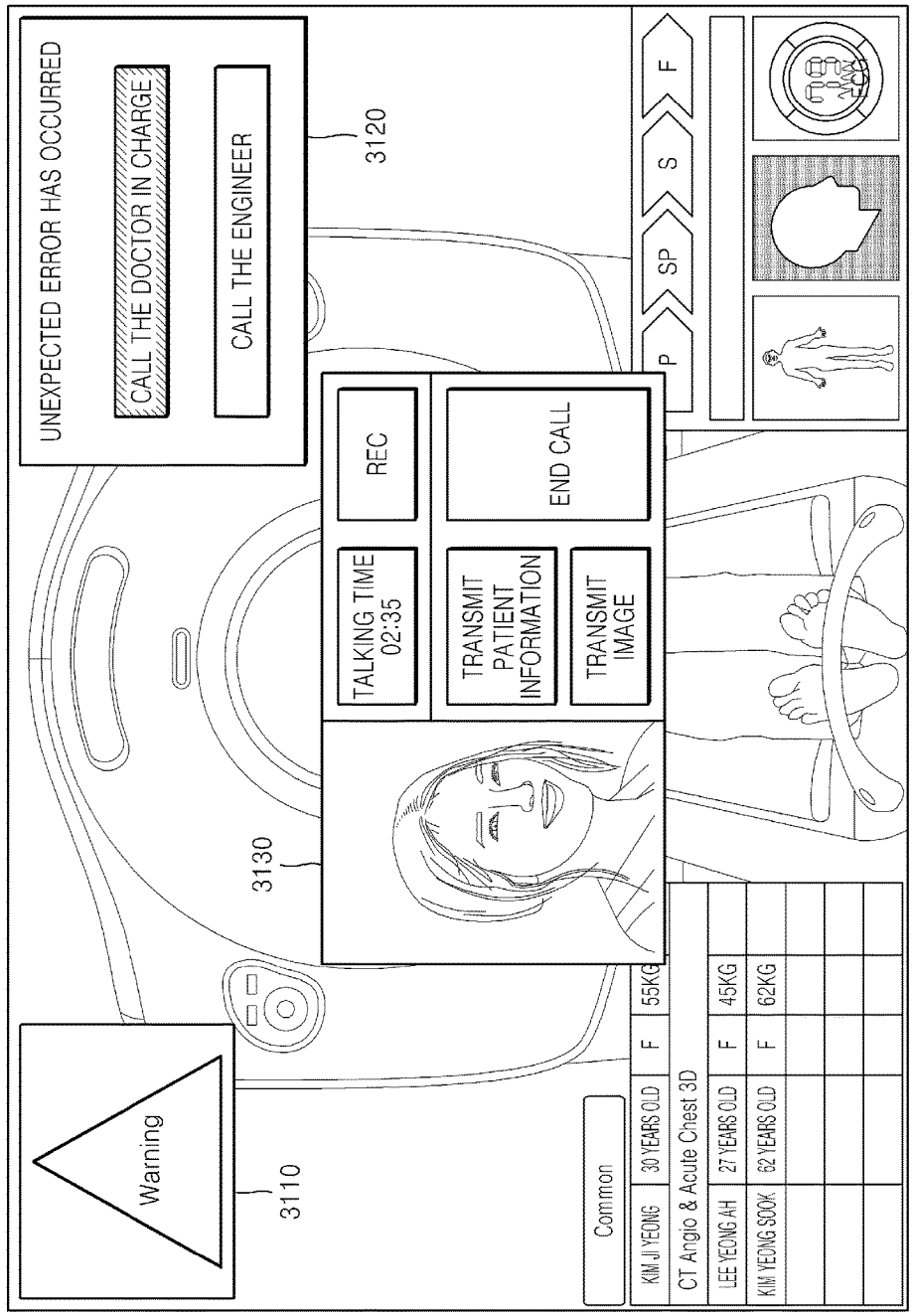
FIG. 31 is a view illustrating various diagnostic information displayed on a console room window, according to still another exemplary embodiment.

FIG. 31 is a view illustrating various pieces of diagnostic information displayed on the console room window 140, according to still another exemplary embodiment. In FIG. 31, operations after the exemplary embodiment of FIG. 30 is performed will be explained.

When the amount of the movement of the object 10 detected by the medical diagnostic system 30 is equal to or greater than a critical value, the medical diagnostic system 30 may stop photographing. Accordingly, the apparatus 100 may determine that the protocol of the medical diagnostic system 30 has been stopped. The apparatus 100 may move the diagnostic information displayed on the information providing area 3010 of FIG. 30 to an information providing area 3110 to be displayed.

Next, the apparatus 100 outputs a message indicating that an error has occurred during the diagnosis to an information providing area 3120 as diagnostic information. The apparatus 100 may output a communication guide menu as diagnostic information when the error has occurred in the medical diagnostic system 30. As shown in FIG. 31, the apparatus 100 provides the communication guide menu to an information providing area 3130.

The apparatus 100 may output a menu guide for a phone call along with a text message indicating that the error has occurred to an information providing area 3120. Next, the apparatus 100 may receive an input that selects a "phone call to a doctor in charge" provided on the information providing area 3120 from the user 5, and may output a communication guide menu for a video call with the doctor in charge to the information providing area 3130.

In detail, the apparatus 100 may provide to the information providing area 3130 a graphic user interface (GUI) for receiving various types of user inputs such as an image of a call-receiver, a talking time, a call-recording button, a patient information transmission button, an image transmission button, and a call end button as a communication guide menu. Accordingly, the user 5 may efficiently perform communication through a network inside and/or outside a hospital by using the communication guide menu.

The exemplary embodiments may be embodied as a program executed in a computer, and may be implemented in a general purpose digital computer by using a computer-readable medium. Also, a structure of data used in the method may be recorded by using various units on a computer-readable medium. It should be understood that program storage devices, as may be used to describe storage devices containing executable computer code for operating various methods according to the exemplary embodiments, shall not be construed to cover transitory subject matter such as carrier waves or signals. Examples of the computer-readable medium may include storage media such as magnetic storage media (e.g., read only memories (ROMs), floppy discs, or hard discs), optically readable media (e.g., compact disk-read only memories (CD-ROMs), or digital versatile disks (DVDs)), etc.

According to a method, apparatus, and recording medium for providing medical information of the exemplary embodiments, a user located in a console room may observe a condition of an inner area of a shield room through a console room window and may receive various diagnostic information through the console room window at the same time. Accordingly, the user may observe the condition of the inner area of the shield room without losing attention.

Also, the console room window may be provided in a transparent unit, and the user may freely adjust an arrangement of a plurality of pieces of diagnostic information. Furthermore, the user may effectively receive diagnostic information by adjusting an arrangement, a size, and a shape of the diagnostic information according to a position of the user and a distance between the user and the console room window. Also, since it is not necessary to dispose a plurality of monitors in the console room, a space of the console room may be efficiently secured.

The foregoing exemplary embodiments and advantages are merely exemplary and are not to be construed as limiting the disclosure. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A method of providing medical information, the method comprising:
    communicating with a medical system, the medical system executing a protocol relating to an object located in a first room;
    receiving, by a device located in a second room, diagnostic information related to the object, the diagnostic information comprising information about progress of the protocol executed on the object, and information about condition of the object; and
    displaying, by the device located in the second room, the diagnostic information onto a transparent display on a console room window, the console room window separating the first room from the second room;
    wherein the displayed diagnostic information and the object in the first room are observable from the second room through the transparent display on the console room window.

2. The method of claim 1, further comprising setting an information providing area on which the diagnostic information is to be displayed on the transparent display, wherein the setting comprises setting at least one from among a size and a position of the information providing area, and
    the displaying comprises displaying the diagnostic information based on the at least one from among the set size and the set position of the information providing area.

3. The method of claim 2, further comprising setting on the console room window an observation area through which the object is observable.

4. The method of claim 3, wherein the setting comprises setting at least a part of the observation area as the information providing area.

5. The method of claim 4, wherein the setting comprises setting an area of the console room window other than the observation area as the information providing area.

6. The method of claim 1, further comprising setting an information providing area on which the diagnostic information is to be displayed on the transparent display, wherein the setting comprises:
    selecting at least one from among a plurality of sub-areas of the console room window; and
    setting the selected at least one sub-area as the information providing area.

7. The method of claim 1, further comprising setting an information providing area on which the diagnostic information is to be displayed on the transparent display,
    wherein the transparent display comprises a plurality of transparent displays arranged adjacent to one another,
    wherein the setting comprises matching at least one from among the plurality of transparent displays to the information providing area.

8. The method of claim 1, wherein the information providing area comprises a plurality of information providing areas,
    wherein the method further comprises determining priorities of the plurality of information providing areas, and
    wherein the displaying comprises displaying a plurality of diagnostic information on the plurality of information providing areas based on at least one from among the priorities of the plurality of information providing areas and orders in which the plurality of diagnostic information are obtained.

9. The method of claim 8, wherein the displaying the diagnostic information comprises determining the plurality of information providing areas on which the plurality of diagnostic information are to be displayed according to importance of the plurality of diagnostic information.

10. The method of claim 1, wherein the information providing area comprises a plurality of information providing areas,
    wherein the method further comprises determining priorities of the plurality of information providing areas, and
    wherein the displaying comprises displaying a plurality of diagnostic information on the plurality of information providing areas based on at least one from among the priorities of the plurality of information providing areas and importance of the plurality of diagnostic information.

11. The method of claim 1, further comprising setting an information providing area on which the diagnostic information is to be displayed on the transparent display,
    wherein the setting comprises setting the information providing area based on a user input.

12. The method of claim 11, wherein the user input is received by using at least one from among a voice recognition sensor, a motion detection sensor, a touch sensor, and a pointing device recognition sensor.

13. The method of claim 1, wherein the displaying comprises adjusting a transparency of the diagnostic information on the console room window based on at least one from among a value of the diagnostic information and a user input.

14. The method of claim 13, wherein the adjusting comprises adjusting the transparency of the diagnostic information based on a type of the diagnostic information.

15. The method of claim 13, wherein the adjusting comprises adjusting the transparency of the diagnostic information based on a position at which the diagnostic information is displayed on the console room window.

16. The method of claim 1, further comprising detecting at least one from among a position of a user and a distance of the user from the console room window.

17. The method of claim 16, wherein the displaying comprises adjusting a size of the information providing area on which the diagnostic information is displayed based on the distance of the user from the console room window.

18. The method of claim 16, wherein the displaying comprises adjusting at least one from among a position and a size of the information providing area on which the diagnostic information is displayed on the console room window based on the position of the user.

19. The method of claim 18, wherein the adjusting comprises reducing the size of the information providing area in response to the detected position of the user which is closer to the information providing area.

20. The method of claim 17, further comprising setting an information providing area on which the diagnostic information is to be displayed on the transparent display,
wherein the information providing area comprises a plurality of information providing areas,
wherein the method further comprises determining priorities of the plurality of information providing areas,
wherein the determining comprises determining the priorities based the position of the user, and
wherein the displaying comprises displaying a plurality of diagnostic information on the plurality of information providing areas based on the determined priorities.

21. The method of claim 1, further comprising setting an information providing area on which the diagnostic information is to be displayed on the transparent display,
wherein the setting comprises setting a substantially entire portion of the console room window as the information providing area.

22. The method of claim 21, further comprising:
capturing an image of an inner area of a shield room in which the object is located; and
displaying the image of the inner area of the shield room on at least a portion of the information providing area.

23. The method of claim 1, wherein the diagnostic information comprises an image obtained by photographing at least a part of the object.

24. The method of claim 1, wherein the diagnostic information comprises an image obtained by photographing a movement of a diagnostic table on which the object is placed.

25. The method of claim 1, wherein the diagnostic information comprises a medical image of the object.

26. The method of claim 1, wherein the diagnostic information comprises an image obtained by photographing an inner area of a gantry in which the object is positioned.

27. The method of claim 1, wherein the diagnostic information comprises a message indicating that a movement of the object is detected, the message being generated in response to an amount of a detected movement of the object which is equal to or greater than a preset value.

28. The method of claim 1, wherein the diagnostic information comprises information about a local memory configured to store the diagnostic information.

29. The method of claim 1, wherein the diagnostic information comprises personal information of the object.

30. The method of claim 1, wherein the diagnostic information comprises a list of patients comprising the object.

31. The method of claim 1, wherein the diagnostic information comprises a control menu for controlling the medical system configured to obtain the diagnostic information of the object.

32. The method of claim 1, wherein the diagnostic information comprises a communication guide menu configured to provide information about communication with an external network,
wherein the method further comprises performing the communication with the external network based on a user input on the communication guide menu.

33. The method of claim 1, wherein the diagnostic information comprises bio-monitoring information about at least a predetermined part of the object.

34. The method of claim 33, wherein the displaying comprises displaying the bio-monitoring information on at least a portion of the information providing area corresponding to the at least a predetermined part of the object.

35. The method of claim 1, wherein the obtaining comprises obtaining the diagnostic information using the medical system comprising at least one from among a magnetic resonance imaging (MRI) system and a computed tomography (CT) system.

36. An apparatus for providing medical information, the apparatus comprising:
a diagnostic information obtaining unit, implemented by at least one processor, configured to communicate with a medical diagnostic system, the medical diagnostic system executing a protocol relating to an object located in a first room, and receive, from the medical diagnostic system, diagnostic information related to the object, the diagnostic information comprising information about progress of the protocol executed on the object, and information about condition of the object;
an area setting unit, implemented by the at least one processor, configured to set an information providing area on which the diagnostic information is to be displayed on a transparent display on a console room window, the console room window separating the first room from a second room in which the apparatus is located; and
a controller, implemented by the at least one processor, configured to control the console room window to display the diagnostic information on the information providing area,
wherein the displayed diagnostic information and the object are observable through the transparent display on the console room window.

37. The apparatus of claim 36, wherein the area setting unit sets at least one from among a size and a position of the information providing area, and
the controller controls the console room window to display the diagnostic information based on the at least one from among the set size and the set position of the information providing area.

38. The apparatus of claim 36, wherein the area setting unit sets on the console room window an observation area through which the console room window is observable.

39. The apparatus of claim 38, wherein the area setting unit sets at least a part of the observation area as the information providing area.

40. The apparatus of claim 39, wherein the information providing area is an area of the console room window other than the observation area.

41. The apparatus of claim 36, wherein the area setting unit selects at least one from among a plurality of sub-areas of the console room window, and sets the at least one selected sub-area as the information providing area.

42. The apparatus of claim 36, wherein the transparent display comprises a plurality of transparent displays arranged adjacent to one another,
wherein the area setting unit matches at least one from among the plurality of transparent displays to the information providing area.

43. The apparatus of claim 36, wherein the information providing area comprises a plurality of information providing areas,
  wherein the area setting unit determines priorities of the plurality of information providing areas, and
  the controller controls the console room window to display a plurality of diagnostic information on the plurality of information providing areas based on at least one from among the priorities of the plurality of information providing areas and orders in which the plurality of diagnostic information are obtained.

44. The apparatus of claim 43, wherein the area setting unit determines the plurality of information providing areas on which a plurality of the diagnostic information are to be displayed according to importance of the plurality of diagnostic information.

45. The apparatus of claim 36, wherein the information providing area comprises a plurality of information providing areas,
  wherein the area setting unit determines priorities of the plurality of information providing areas, and
  the controller controls the console room window to display a plurality of diagnostic information on the plurality of information providing areas based on at least one from among the priorities of the plurality of information providing areas and importance of the plurality of diagnostic information.

46. The apparatus of claim 36, further comprising a user input unit configured to receive a user input,
  wherein the area setting unit sets the information providing area based on the user input.

47. The apparatus of claim 46, wherein the user input is received by using at least one from among a voice recognition sensor, a motion detection sensor, a touch sensor, and a pointing device recognition sensor.

48. The apparatus of claim 36, wherein the controller controls the console room window to adjust a transparency of the diagnostic information on the console room window based on at least one from among a value of the diagnostic information and a user input.

49. The apparatus of claim 48, wherein the controller controls the console room window to adjust the transparency of the diagnostic information based on a type of the diagnostic information.

50. The apparatus of claim 48, wherein the controller controls the console room window to adjust the transparency of the diagnostic information based on a position at which the diagnostic information is displayed on the console room window.

51. The apparatus of claim 36, further comprising a sensing unit configured to detect at least one from among a position of a user and a distance of the user from the console room window.

52. The apparatus of claim 51, wherein the area setting unit adjusts a size of the information providing area on which the diagnostic information is displayed based on the distance of the user from the console room window,
  wherein the controller controls the console room window to display the diagnostic information on the information providing area having the adjusted size.

53. The apparatus of claim 51, wherein the area setting unit adjusts at least one from among a size and a position of the information providing area on which the diagnostic information is displayed on the console room window based on the position of the user,
  wherein the controller controls the console room window to display the diagnostic information on the information providing area having the at least one from among the adjusted size and the adjusted position.

54. The apparatus of claim 53, wherein the area setting unit reduces the size of the information providing area in response to the detected position of the user which is closer to the information providing area,
  wherein the controller controls the console room window to display the diagnostic information on the information providing area having the reduced size.

55. The apparatus of claim 52, wherein the information providing area comprises a plurality of information providing areas,
  wherein the area setting unit determines priorities of the plurality of information providing areas based on the position of the user, and
  wherein the controller controls the console room window to display a plurality of diagnostic information on the plurality of information providing areas based on the determined priorities.

56. The apparatus of claim 36, wherein the area setting unit sets a substantially entire portion of the console room window as the information providing area.

57. The apparatus of claim 56, further comprising a sensing unit configured to capture an image of an inner area of a shield room in which the object is located,
  wherein the controller controls the console room window to display the image of the inner area of the shield room on at least a portion of the information providing area.

58. The apparatus of claim 36, wherein the diagnostic information comprises an image obtained by photographing at least a part of the object.

59. The apparatus of claim 36, wherein the diagnostic information comprises an image obtained by photographing a movement of a diagnostic table on which the object is placed.

60. The apparatus of claim 36, wherein the diagnostic information comprises a medical image of the object.

61. The apparatus of claim 36, wherein the diagnostic information comprises an image obtained by photographing an inner area of a gantry in which the object is positioned.

62. The apparatus of claim 36, further comprising a sensing unit configured to determine whether an amount of a detected movement of the object is equal to or greater than a preset value,
  wherein the diagnostic information comprises a message indicating that a movement of the object is detected, the message being generated according to a result of a determination of the sensing unit.

63. The apparatus of claim 36, wherein the diagnostic information comprises information about a local memory configured to store the diagnostic information.

64. The apparatus of claim 36, wherein the diagnostic information comprises personal information of the object.

65. The apparatus of claim 36, wherein the diagnostic information comprises a list of patients comprising the object.

66. The apparatus of claim 36, wherein the diagnostic information comprises a control menu for controlling a medical system configured to obtain the diagnostic information of the object.

67. The apparatus of claim 36, wherein the diagnostic information comprises a communication guide menu configured to provide information about communication with an external network,
  wherein the apparatus performs the communication with the external network based on a user input on the communication guide menu.

68. The apparatus of claim 36, wherein the diagnostic information comprises bio-monitoring information about at least a predetermined part of the object.

69. The apparatus of claim 68, wherein the controller controls the console room window to display the bio-monitoring information on at least a portion of the information providing area corresponding to the at least a predetermined part of the object.

70. The apparatus of claim 36, wherein the diagnostic information obtaining unit obtains the diagnostic information using a medical system comprising at least one from among a magnetic resonance imaging (MRI) system and a computed tomography (CT) system.

71. A computer-readable recording medium having embodied thereon a program for executing the method of claim 1.

72. An information providing apparatus comprising:
at least one processor operable to read and operate according to instructions within a computer program; and
at least one memory operable to store at least portions of the computer program for access by the at least one processor;
wherein the computer program includes algorithms which, when executed by the at least one processor, cause the at least one processor to perform:
communicating with a medical diagnostic system, the medical diagnostic system executing a protocol relating to an object located in a first room;
receiving, from the medical diagnostic system, diagnostic information related to the object, the diagnostic information comprising information about progress of the protocol executed on the object, and information about condition of the object; and
displaying the diagnostic information onto a transparent display on a console room window, the console room window separating the first room from a second room in which the apparatus is located,
wherein the displayed diagnostic information and the object are observable through the transparent display on the console room window.

73. The information providing apparatus of claim 72, wherein the algorithms further cause the at least one processor to perform adjusting the information providing area on the console room window based on at least one of a user command and a position of a user.

* * * * *